United States Patent [19]

Szmuszkovicz

[11] 4,156,733
[45] May 29, 1979

[54] N-(2-AMINOCYCLOPENTYL) ALKANOYLANILIDES

[75] Inventor: Jacob Szmuszkovicz, Kalamazoo, Mich.

[73] Assignee: The Upjohn Company, Kalamazoo, Mich.

[21] Appl. No.: 879,378

[22] Filed: Feb. 21, 1978

Related U.S. Application Data

[60] Division of Ser. No. 777,599, Mar. 15, 1977, abandoned, which is a continuation-in-part of Ser. No. 746,191, Nov. 30, 1976, abandoned.

[51] Int. Cl.$^2$ .................. A61K 31/40; A61K 31/445; C07D 207/12; C07D 211/06
[52] U.S. Cl. ................................. 424/274; 260/326.4; 424/267; 546/231; 546/234; 546/232
[58] Field of Search ................ 424/324, 267, 274; 260/562 R, 326.4

[56] References Cited

U.S. PATENT DOCUMENTS 3,510,492  5/1970  Szmuszkovicz ................ 260/293.79

*Primary Examiner*—Stanley J. Friedman
*Attorney, Agent, or Firm*—John T. Reynolds

[57] ABSTRACT

N-(2-Aminocyclopentyl)N-alkanoylanilides and their 2-N-oxides of the formula

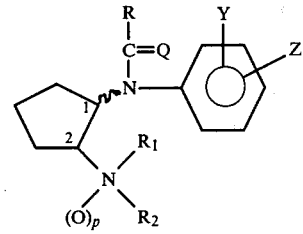

e.g., trans-3,4-dichloro-N-[2-(dimethylamino)cyclopentyl]propionanilide, and their pharmacologically acceptable salts, have been found to possess potent Central Nervous System anti-depressant properties. Many of them are new.

These compounds are promising anti-depressant drugs which are characterized by a better therapeutic ratio than imipramine, and long acting activity which may allow longer durations between administrations, e.g., once a day. Pharmaceutical compositions containing these compounds and a process for treating conditions of depression with these compositions are disclosed.

9 Claims, No Drawings

N-(2-AMINOCYCLOPENTYL) ALKANOYLANILIDES

This application is a division of U.S. Pat. application Ser. No. 777,599 filed Mar. 15, 1977, which is a continuation-in-part of U.S. Pat. application Ser. No. 746,191, filed Nov. 30, 1976.

INTRODUCTION

This invention relates to amino-cycloaliphatic amides which have central nervous system pharmaceutical utility. More particularly this invention provides some new pharmaceutical preparations containing cis and trans N-(2-aminocyclopentyl)-N-alkanoylanilide compounds or their pharmacologically acceptable salts which have been found to have potent central nervous system (CNS) antidepressant properties which makes them useful as antidepressant drugs, when formulated into useful pharmaceutically useable composition forms, and administered in appropriate dosages.

BACKGROUND OF THE INVENTION

W. G. Stoll et al., in *Helvetica Chemica Acta*, Vol. 34, (1951), pp. 1937 to 1943 disclose N-[2-(dimethylamino)-cyclohexyl]aniline and procedures for making it from N-(2-hydroxycyclohexyl)aniline and suggest that the compounds therein have antihistamine pharmacological properties, but nothing is said about the compounds of this invention or their use as antidepressant drugs.

J. W. Lewis et al., in an article entitled "The Reactions of Aromatic Nitroso-compounds with Enamines. Part I. The Reaction of Nitrosobenzene with 1-Morpholin-1-cyclohexene" in *J. Chem. Soc.* (London) (1972), Perkins Transactions I, Part III, pp. 2521–2524 discloses inter alia N-(2morpholin-1-ylcyclohexyl)-phenylhydroxylamine and its hydrochloride salt, but it does not disclose or suggest the alkanoyl-anilides of this invention or their antidepressant properties.

J. W. Lewis et al., in an article entitled "Chemistry and Biological Activity of N-Substituted Hydroxylamines" in *J. Pharmaceutical Sciences*, December, 1974, Vol. 63, No. 12, pp. 1951–1953 discloses some N-Arylhydroxylamines such as N-[2-(N-pyrrolidinyl)cyclohexyl]-N-phenylhydroxylamine but these do not have useful CNS properties. Diuretic activity is alleged therein for the alcohols such as [2-(N-piperidinylcyclohexyl]-(4-methoxyphenyl)methanol and when the alcohol is acetylated CNS depressant activity is said to appear. It also discloses the reaction of propionyl chloride with N-[2-(N-piperidinyl)-1,1-dimethylethyl]-N-phenylhydroxylamine to form the N-chloro compound which is then converted to a mixture of chlorinated aniline derivatives. That publication does not teach the compounds disclosed herein, how to make them, nor does it suggest the antidepressant properties which have been found for the compounds disclosed and claimed herein.

Szmuszkovicz U.S. Pat. No. 3,510,492 discloses and claims some 2-anilino- and 2-anilinomethylcycloalkylamines which are useful as antidiabetic drugs in that they can be administered in low dosages for reducing blood sugar. However, that patent in column 2, structure IV generically suggests some of the formula I compounds of the pharmaceutical preparations and use process of this invention as chemical intermediates en route to the 2-anilinocycloalkyl amines thereof, but it does not suggest any end product practical utility for those structure IV compounds.

OBJECTS OF THE INVENTION

It is an object of this invention to provide some new N-(2-aminocyclopentyl)alkanoylanilides which have been found to have promising antidepressant drug properties.

It is a more specific object of this invention to provide new N-(2-aminocyclopentyl)alkanoylanilides which are useful as antidepressant drugs the preferred compounds having a better therapeutic ratio than imipramine and longer lasting activity which allows longer durations between administrations.

It is another object of this invention to provide compositions, useful in pharmaceutical dosage unit form, for treating conditions of depression in mammals including humans comprising an N-(2-aminocyclopentyl)alkanoylanilides as described herein, or a pharmacologically acceptable salt thereof in a pharmaceutical carrier.

It is another object of this invention to provide a process for treating conditions of depression in mammals including humans with these compositions containing an N-(2-aminocyclopentyl)alkanoylanilide, or a pharmacologically acceptable salt thereof.

Other objects, aspects and advantages of this invention will be apparent from reading the specification and claims which follow.

SUMMARY OF THE INVENTION

Briefly, this invention provides pharmaceutical preparations of some cis and trans-N-(2-aminocyclopentyl)N-alkanoylanilides of the formula

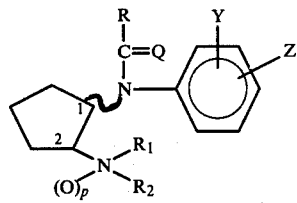

and their pharmacologically acceptable salts, wherein p, Q, R, $R_1$, $R_2$, Y and Z are as defined hereinbelow, which have been found to possess potent central nervous system (CNS) antidepressant properties. A preferred example for this use is trans-3,4-dichloro-N-[2-(dimethylamino)cyclopentyl]propionanilide. This invention also includes these compounds (I) which are new, per se, and their acid addition salts, especially their pharmacologically acceptable salts. These compounds are useful, in appropriate pharmaceutical dosage unit form, for administration of humans in dosages of from 1–100 mg. per day as part of the therapy in treating conditions of depression. In standard laboratory animals used to determine these properties these compounds suggest fast onset of the antidepressant characteristics of the drug, the preferred compounds having in addition, a better therapeutic ratio (higher activity and/or lower toxicity) than a standard antidepressant drug, imipramine, in standard laboratory tests, and longer duration of activity of the test compound in the test animal. These characteristics of these compounds will make them useful for the administration of these compounds as antidepressant drugs in smaller amount and/or for longer durations between administration, e.g., once a day, for a given desired antidepressant response.

This invention also includes a process for treating depression with these compositions containing these above formula I compounds, or pharmaceutically acceptable salts thereof, and a pharmaceutical carrier, which compositions are useful in dosage unit form for treating conditions of depression in mammals including humans.

DETAILED DESCRIPTION OF THE INVENTION

More specifically, one aspect of this invention provides new pharmaceutical preparations containing compounds of the formula

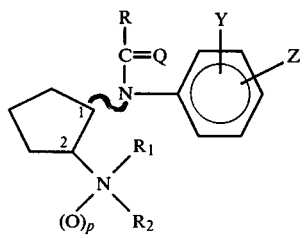

wherein the wavy line (∼) on the 1-position of the cyclopentyl ring denotes cis- or trans-configuration relative to the amino group in the 2-position of the cyclopentyl ring p is zero or 1;
Q is oxygen or sulfur;
R is $C_1$ $C_3$-alkyl, $C_3$ to $C_6$-cycloalkyl, vinyl (-CH=CH$_2$), ethoxy or methoxymethyl;
$R_1$, taken separately, is $C_1$ to $C_3$-alkyl;
$R_2$, taken separately, is $C_1$ to $C_3$-alkyl, and when $R_1$ is $C_1$ to $C_3$-alkyl, $R_2$ can be
-CH$_2$CH$_2$N(CH$_3$)$_2$,
-CH$_2$CH$_2$CH$_2$N(CH$_3$)$_2$,
-CH$_2$C$_6$H$_5$(benzyl),
-CH$_2$CH$_2$-C$_6$H$_5$, or
$C_3$-$C_6$(allylic)alkenyl and when $R_1$ and $R_2$ are taken together with the nitrogen to which they are bonded they complete an N-pyrrolidinyl or an N-piperidinyl ring;
each of Y and Z is selected from the group consisting of hydrogen, a halogen having an atomic number of from 9 to 35, trifluoromethyl, $C_1$ to $C_2$-alkyl, azido(-N$_3$), and $C_1$ to $C_2$-alkyloxy, and when Y is trifluoromethyl or azido Z is hydrogen, when Y is $C_1$ to $C_2$-alkyloxy and Z is hydrogen the $C_1$ to $C_2$-alkyloxy is in the 3-position, when Y and Z are both halogens or $C_1$ to $C_2$-alkyloxy, they are present in 3- and 4- or 3- and 5- positions, and the acid addition salts thereof, preferably the pharmacologically acceptable acid addition salts thereof. On occasion the compounds or their acid addition salts in their crystalline state are isolated as solvates, i.e., with a discreet quantity of solvent, e.g., water, methanol, and the like, associated physically, and thus the solvent is removable without effective alteration of the chemical entity per se and are included with the compounds per se herein.

In the above formula I compounds the term "$C_1$ to $C_3$-alkyl" means methyl, ethyl, n-propyl and isopropyl; the term "$C_3$ to $C_6$-cycloalkyl" means cyclopropyl, cyclobutyl, cyclopentyl and cyclohexyl groups; the term "$C_3$ to $C_6$-(allylic)alkenyl" includes the non-adjacent double bond groups, e.g., allyl, 2-butenyl and 2-methyl-2-butenyl, 2-pentenyl, 3-methyl-2-pentenyl, and 2-hexenyl groups; and the halogens having atomic numbers of from 9 to 35 are fluorine, chlorine and bromine.

The preferred compounds of this invention are those of the trans configuration.

A preferred subgroup of the above compounds are the pharmaceutical preparation forms thereof are those wherein R is ethyl; $R_1$ and $R_2$ are each $C_1$ to $C_3$ alkyl; and at least one of Y and Z are halogen having an atomic number of from 9 to 35 preferably in the 3- and 4-positions, trifluoromethyl in the 3-position, or methyl in the 3- or 4- position in combination with one of the above halogens at the adjacent 3- or 4- position, and the pharmacologically acceptable salts thereof. Examples of such compounds include the following:

3,4-dichloro-N-[2-(dimethylamino)cyclopentyl]propionanilide;
3-trifluoromethyl-N-[2-(dimethylamino)cyclopentyl]-propionanilide,
3,4-dichloro-N-[2-(diethylamino)cyclopentyl]propionanilide,
3-chloro-4-methyl-N-[2-(dimethylamino)cyclopentyl]-propionanilide,
4-chloro-4-methyl-N-[2-(dimethylamino)cyclopentyl]-propionanilide,
3-chloro-N-[2-(dimethylamino)cyclopentyl]propionanilide,
4-chloro-N-[2-(dimethylamino)cyclopentyl]propionanilide,
3-bromo-N-[2-(dimethylamino)cyclopentyl]propionanilide, and
3-fluoro-N-[2-dimethylamino)cyclopentyl]propionanilide, especially these compounds in the trans configurations, and the pharmacologically acceptable salts thereof.

Another preferred sub-group of the above compounds are those wherein R is $C_1$ to $C_3$-alkyl, preferably ethyl, $R_1$ and $R_2$ are taken together with the nitrogen to which they are bonded to complete an N-pyrrolidinyl or N-piperidinyl ring, and at least one of Y and Z is a halogen having an atomic number of from 9 to 35 in the 3- and/or 4- positions. Examples of such compounds include:

3-fluoro-N-[2-(N-pyrrolidinyl)cyclopentyl]propionanilide,
3,4-dichloro-N-[2-(N-piperidinyl)cyclopentyl]propionanilide;
3-bromo-N-[2-(N-pyrrolidinyl)cyclopentyl]propionanilide.
4-chloro-N-[2-(N-pyrrolidinyl)cyclopentyl]propionanilide,
3,4-dichloro-N-[2-(N-pyrrolidinyl)cyclopentyl]propionanilide,
3,4-difluoro-N-[2-(N-pyrrolidinyl)cyclopentyl]propionanilide, and
3,4-dibromo-N-[2-(N-pyrrolidinyl)cyclopentyl]propionanilide, especially these compounds in their trans configuration and the pharmacologically acceptable salts thereof.

Another preferred sub-group of the above compounds are those wherein R is $C_3$ to $C_6$-cycloalkyl, $R_1$ and $R_2$ are $C_1$ to $C_3$-alkyl, and at least one of Y and Z are halogen having an atomic number of from 9 to 35 in the 3- or 4- position, trifluoromethyl in the 3-position, or methyl in the 3- or 4- position in combination with one of the above halogens in the adjacent 3- or 4-positions, and the pharmacologically acceptable salts thereof. Examples of such compounds include:

3,4-dichloro-N-[2-dimethylaminocyclopentyl]cyclobutanecarboxanilide, 3,4-dichloro-N-[2-dimethylaminocyclopentyl]cyclohexanecarboxanilide,
3-bromo-4-methyl-N-[2-dimethylaminocyclopentyl]cyclobutanecarboxanilide,
3,4-dichloro-N-[2-dimethylaminocyclopentyl]cyclopropanecarboxanilide,
3-trifluoromethyl-N-[2-diethylaminocyclopentyl]cyclopropanecarboxanilide,
3,4-dibromo-N-[2-diethylaminocyclopentyl]cyclopropanecarboxanilide,
3-chloro-4-methyl-N-[2-dimethylaminocyclopentyl]cyclopropanecarboxanilide,
3-bromo-4-methyl-N-[2-dimethylaminocyclopentyl]cyclohexanecarboxanilide,
3-trifluoromethyl-N-[2-dimethylaminocyclopentyl]cyclohexanecarboxanilide, and
the pharmacologically acceptable salts thereof.

Examples of acid addition salts, including pharmacologically acceptable salts of the above formula I compounds include those of hydrochloric, methanesulfonic, hydrobromic, sulfuric, acetic, cyclohexanesulfamic, p-toluenesulfonic, succinic, β-naphthalenesulfonic, maleic, fumaric, citric, lactic and oxalic acids.

To use these new compounds in pharmaceutical antidepressant drug product form they are compounded or formulated into usual pharmaceutical compositions, e.g., oral dosage forms such as tablets, powders, capsules and solutions or suspensions in a suitable solvent or suspending vehicle, and parenteral dosage forms such as dry powder in a sterile sealed container to be mixed with a sterile solvent just prior to administration, sterile solutions or suspensions in water or other suitable solvents or suspending agents, to provide a convenient means for administering daily doses of from about 1 mg. to about 100 mg., preferably 10 to 90 mg., of the formula I compound or its pharmacologically acceptable salt, depending upon the potency of the formula I compound, the condition being treated, the weight of the patient and other factors of concern to the patient's physician.

The formula I compounds where Q is oxygen (=O) and p is zero can be prepared by (a) heating a mixture of a compound of the formula

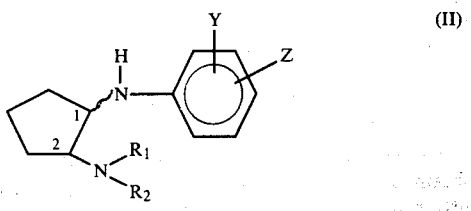

wherein $R_1$, $R_2$, Y and Z are as defined above, and an anhydride of the appropriate organic carboxylic acid of the formula R-COOH on a steam bath, or at an equivalent temperature, for a time sufficient to form the N-acylated product of the formula I where R is as defined above, Q is oxygen and p is zero, (b) adding an aqueous medium to the step (a) reaction mixture in an amount sufficient to decompose excess anhydride therein, (c) adding an alkali metal hydroxide or its equivalent to the step (b) reaction mixture in an amount sufficient to neutralize excess acid present therein and to make the mixture pH basic, (d) extracting the N-acylated product (I) into a water immiscible organic liquid solvent, e.g. ether solvents such as diethyl ether, tetrahydrofuran or dioxane, or chloroform, carbon tetrachloride, methylene chloride, ethylene dichloride, or the like, (e) separating the organic liquid phase containing the N-acylated product (I) from the aqueous phase, and (f) recovering the corresponding N-acylated compound (I) from the organic liquid phase, usually after washing the organic liquid phase one or more times with aqueous media such as sodium chloride solution, sodium bicarbonate solution or water to extract components soluble in those aqueous media, separating the aqueous phases, drying the washed organic phase with drying agents such as magnesium sulfate or sodium or calcium sulfate, and then evaporating off the organic solvent. Further purification can be done by forming an acid addition salt of the N-acylated amide product (I) and then re-crystallizing the amide salt from an appropriate solvent or mixture of solvents.

These formula I compounds, immediately above, can also be prepared by (a) adding a solution of the appropriate carboxylic acid halide R-C(O)-X where R is as defined above and X is chloride or bromide to a cooled (−5° to +10° C.) mixture of the diamine (II), and a tertiary amine which will form a tertiary amine chloride or bromide salt in the mixture, e.g., a $C_1$ to $C_4$-trialkylamine, e.g., trimethylamine, triethylamine, tributylamine, or pyridine, lutidine, N,N-dimethylaniline or the like, in an organic liquid solvent for the mixture such as an ether solvent such as diethyl ether, THF, dioxane or the like, while agitating the mixture until the corresponding N-acylated compound (I) is formed, (b) adding an aqueous alkali metal bicarbonate solution to the reaction mixture of step (a), (c) separating the aqueous from the organic liquid phases, (d) washing the organic liquid phases with aqueous wash liquids as described above, (e) drying the organic phase, and (f) recovering the N-acylated compound (I) from the resulting organic liquid mixture. The N-acylated amide compound (I) can be further purified by formation of an acid addition salt thereof, e.g., the hydrochloric acid, or maleic acid addition salt thereof, and re-crystallization of the amide salt from an appropriate solvent or solvent mixture.

The formula I compounds which do not contain a reactive aliphatic carbon-to-carbon double bond in the molecule, that is, those wherein Q is oxygen (=O) and p is zero, can be converted to their N-oxides by reaction of such formula I aminoamide or its salt with a percarboxylic acid by known procedures to obtain the corresponding formula I compound where p is 1.

The corresponding N-thioacyl amino anilide compounds can be prepared by heating to reflux the corresponding N-acyl(C=O) amino anilide (formula I compound) with a thiolating agent such as phosphorus pentasulfide or diethyl-dithiophosphate $(P(S)SH(OC_2H_5)_2)$ in an appropriate solvent such as pyridine for a time sufficient to effect replacement of the acyl oxygen atom with sulfur, and then recovering and purifying the N-thioacyl aminoanilide compound by known procedures. If the N-oxides of the Q is S compounds are to be made, the N-oxide is prepared first and the resulting N-oxide is thiolated as described above to form the formula I compound where Q is =S and p is 1.

Further exemplification of these process procedures appear in the detailed examples.

The trans-diamine starting materials (II) of the formula

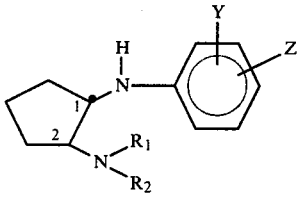

wherein $R_1$, $R_2$, Y and Z are as defined above can be prepared by reacting 1,2-cyclopentene oxide (IIIa)

with the selected $HNR_1R_2$ amine in water to form the trans-2-aminocyclopentanol of the formula IIIb

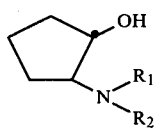

which amino-alcohol (IIIb) is treated with sodium hydride and then with methanesulfonyl chloride to form unrecovered mesylate of the formula IV

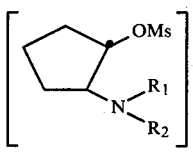

wherein Ms denotes $CH_3SO_2$-group and that reaction mixture is treated with the selected substituted aniline of formula V

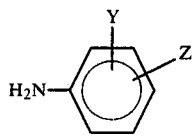

to form the diamine (II). Examples of this procedure are given hereinbelow in the detailed descriptions.

Examples of the carboxylic acid anhydrides which can be used to prepare the compounds of this invention include acetic anhydride, pripionic anhydride, isobutanoic anhydride, n-butanoic anhydride, cyclopropanecarboxylic acid anhydride, acrylic acid anhydride, and the like. The preferred anhydride is propionic acid anhydride. The carboxylic acid haides are exemplified by acetyl chloride or bromide, propionyl chloride or bromide, acryloyl chloride or bromide, cyclohexanecarbonyl chloride or bromide, n- and isobutanoylchloride or bromide, cyclopropanecarbonyl chloride or bromide, ethyl formate, methoxyacetyl chloride or bromide and the like. We have found that, in general, the most potent antidepressant compounds are made from those compounds having an N-propionyl moiety, so that in the formula I compounds R is preferably ethyl.

When it is desired that the formula I have an allyl group in the $R_2$ position an alternate method can also be used: the amino-amide is prepared as described above using an alkyl benzylamine to form the amino-alcohol (IIIb), and that amino-alcohol is carried through the intermediate (IV), and (V) reactions to form the diamine. The resulting diamine is then hydrogenated catalytically, preferably in the presence of palladium on carbon catalyst, to remove the benzyl group in the $R_2$ position and form the transdiamine of the formula VI.

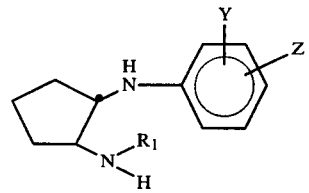

The trans-diamine (VI) is then reacted with the allylic alkenyl chloride or bromide to form the diamine of the formula VII

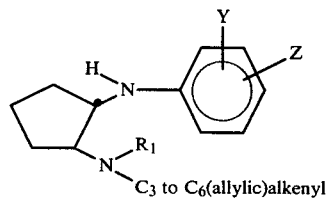

which diamine (VII) is used as an intermediate in a reaction with the selected carboxylic acid anhydride or acid chloride or bromide as described above, to form the N-acylated product of the formula

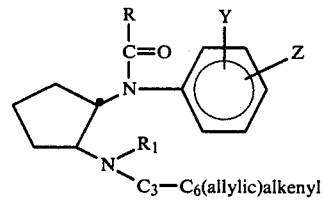

in which formulas Ia, IIIb, IV, V, VI, VII and VIII, R, $R_1$, Y and Z are as defined above.

Preparation of cis amino amide compound of invention:

The method of J. W. Lewis et al., *J. Pharm. Sci.*, 63, 1951 (1974) using 1-dialkylaminocyclopentene (enamine) and nitrosoaryl as starting materials can be used to obtain cis-1,2-diaminocyclopentane which is subsequently reacted with carboxylic acid anhydride or carboxylic acid halide as described above to give the product amino-amide.

A preferred method, which is that used for this invention involves reaction of cyclopentene oxide with an aniline in the presence of strong acid to give the compound of formula

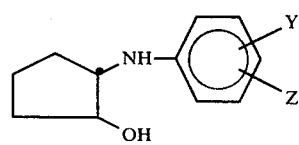

which is subsequently reacted with carboxylic acid anhydride followed by reaction with base to isolate the compound of formula

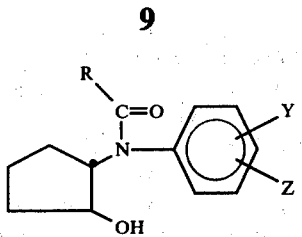

oxidation of the alcohol leads to the compound of formula

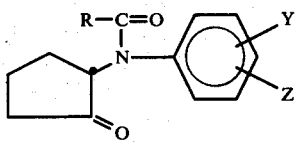

which when reacted with primary or secondary amine and a reducing agent such as sodium cyanoborohydride, and the like, gives a compound of the formula

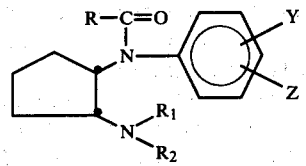

wherein $R_2$ is not $C_3$-$C_6$(allylic)alkenyl. Cis compounds wherein $R_2$ is $C_3$ to $C_6$-(allylic)alkenyl can be prepared analogously to the corresponding trans compounds; in that case a primary amine is used with the reducing agent followed by the allylic alkenyl chloride or bromide.

The thio analogs of such cis amino-amides can be prepared as described earlier in this specification.

Examples of additional useful compounds of formula I of this invention include the following compound, preferably in their trans-configuration N-[2-(dimethylamino)cyclopentyl]propionanilide,
3-methyl-N-[2-(dimethylamino)cyclopentyl]propionanilide,
3-methoxy-N-[2-(dimethylamino)cyclopentyl]propionanilide,
3,4-dichloro-N-{2-[N-methyl-N-(2-dimethylaminoethyl)amino]cyclopentyl}propionanilide,
3,4-dichloro-N-{2-[N-methyl-N-(3-dimethylaminopropyl)amino]cyclopentyl}propionanilide,
N-[2-(dimethylamino)cyclopentyl]acetanilide,
N-[2-(dimethylamino)cyclopentyl]butyranilide,
3-trifluoromethyl-N-[2-(N-methyl-N-benzylamino)-cyclopentyl]propionanilide,
3,4-dibromo-N-{2-[N-ethyl-N-(2-phenylethyl)amino]cyclopentyl}propionanilide,
3-chloro-4-methyl-N-[2-(N-methyl-N-allylamino)cyclopentyl]propionanilide,
4-bromo-3-methyl-N-[2-(N-pyrrolidinyl)cyclopentyl]propionanilide,
3,4-difluoro-N-{2-[N-methyl-N-(2-dimethylaminoethyl)amino]cyclopentyl}propionanilide,
3-chloro-4-fluoro-N-[2-(dimethylamino)cyclopentyl]propionanilide,
3,4-dibromo-N-[2-(dimethylamino)cyclopentyl]propionanilide,
3,4-dimethyl-N-[2-(dimethylamino)cyclopentyl]propionanilide,
3,4-dichloro-N-[2-(dimethylamino)cyclopentyl]butyranilide,
3,4-dichloro-N-[2-(dimethylamino)cyclopentyl]-N-cyclopropanecarboxanilide,
3,4-dichloro-N-[2-(dimethylamino)cyclopentyl]thiopropionanilide,
3,4-dichloro-N-[2-(dimethylamino)cyclopentyl]-N-acrylanilide,
3,4-dichloro-N-[2-(dimethylamino)cyclopentyl]isobutyranilide,
3-bromo-N-[2-(N-methyl-N-benzylamino)cyclopentyl]butyranilide,
3-chloro-4-fluoro-N-[2-(N-pyrrolidinyl)cyclopentyl]-cyclopropanecarboxanilide,
3,5-dibromo-N-[2-(N-methyl-N-2-phenylethylamino)cyclopentyl]propionanilide,
3,4-dichloro-N-[2-dimethylaminocyclopentyl]methoxyacetanilide,
3,4-dichloro-N-[2-dimethylaminocyclopentyl]carbethoxyanilide,
3-methyl-4-chloro-N-[2-diethylaminocyclopentyl]propionanilide,
3-trifluoromethyl-N-{2-(N-methyl-N-2-butenyl]aminocyclopentyl}cyclohexanecarboxanilide,
3-ethoxy-4-bromo-N-[2-dimethylaminocyclopentyl]propionanilide,
4-azido-N-[2-(dimethylamino)cyclopentyl]propionanilide, and the like, the 2-N-oxides of the above compounds which do not contain aliphatic unsaturation, and their acid addition salts.

If desired the formula I compounds of this invention can be resolved into their respective d- and l-optical isomers by methods known in the art. In this case the optical resolution can be done by at least two different routes. The resolving agents by either route are any of the known resolving agents such as optically active camphorsulfonic acid, bis-p-toluoyltartaric acid, tartaric acid, and diacetyl tartaric acid which are commercially available and which are commonly used for resolution of amines (bases) as for example in *Organic Syntheses,* Coll. Vol. V., p. 932 (1973), resolution of R-(+) and S-(−)-α-phenylethylamine with (+)-tartaric acid.

By the first method for resolving the compounds of this invention, for example, one of the amino amide compounds can be converted into its optically active diastereomeric salts by reaction with an optically active acid—examples of which are mentioned above—in a manner standard in the isomer resolution art. These diastereomeric salts can then be separated by conventional means such as differential crystallization. Diastereomeric salts have different crystallization properties, which are taken advantage of this separation. On neutralization each diastereomeric salt with aqueous base the corresponding optically active of the free amino-amide can be obtained, each of which can subsequently and separately be converted as previously described in the examples to the desired acid addition salt.

By the second method, which in the case of some of these compounds is preferred, the formula I compound can be made into their respective d- and l-isomers, by first resolving cis- or trans-1,2-cycloaliphatic unsymmetrically substituted diamine into its respective d- and l-isomers by treatment with the resolving agent, crystallization, separation, and regeneration of the respective trans-d-diamine, trans-l-diamine, or the cis-d-diamine and cis-l-diamine, and then reacting the respective resolved diamine starting matrial with the desired carboxylic acid anhydride or halide to form the respective cisor trans-d- or l-compound of formula I, which can then be converted to any desired pharmaceutically acceptable acid addition salt by procedures exemplified above.

If the acid addition salt used to extract the formula I compound from its reaction mixture is not itself pharmacologically acceptable, the free amino-amide base (I) can be prepared from the acid salt, and thereafter converted to a pharmacologically acceptable salt, by known procedures.

In the use of these compounds of formula I as antidepressant drugs the selected compound of formula I which is to be the antidepressant active ingredient is mixed with suitable pharmaceutical diluents to obtain pharmaceutical compositions suited for oral, parenteral and rectal use in dosage unit form, e.g., tablets, powder packets, cashets, dragees, capsules, solutions, suspensions, sterile injectable forms, suppositories, bougies, and the like. Suitable diluents or carriers such as carbohydrates (lactose), proteins, lipids, calcium phosphate, corn starch, stearic acid, methylcellulose and the like may be used as carriers or for coating purposes. Water and oils, e.g., coconut oil, sesame oil, safflower oil, cottonseed oil, peanut oil may be used for preparing solutions or suspensions of the active drug. Sweetening, coloring and flavoring agents may be added. The specifications for the dosage unit forms of these formula I compounds will vary somewhat from compound to compound and dependent upon the physical characteristics of the formula I compound or its pharmacologically acceptable salt, the particular patient's weight and age, and the particular effect sought to be achieved. The pharmaceutical dosage unit forms of these compounds are prepared in accordance with the preceding general description to provide from about 1 to about 100 mg. of the formula I compound or its pharmacologically acceptable salt per dosage unit form. The amount of the formula I compound prescribed in pharmaceutical dosage unit form is that amount sufficient to obtain in the patient a relief from the condition of depression effect at a non-toxic dosage level.

The following detailed procedures and examples further describe and illustrate how to make and use the starting amines and the compounds of this invention. All temperatures are in degrees Centigrade unless otherwise indicated. For brevity, the term THF means tetrahydrofuran, NMR means nuclear magnetic resonance spectrum, IR means infrared spectrum, UV means ultraviolet spectrum, ether means diethyl ether, NaOH means sodium hydroxide, MgSO4 means anhydrous magnesium sulfate, and MeOH means methanol.

I. General procedure for the preparation of trans-2-aminocycloalkanols

The procedure is exemplified by the preparation of trans-2-dimethylaminocyclopentanol. Analogs are listed in Table I. All compounds listed have NMR, IR, UV and mass spectra consistent with the respective structures.

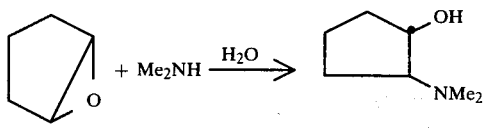

A mixture of cyclopentene oxide (188 g., 2.24 moles) and aqueous dimethylamine (40%, 750 ml., 6.67 moles) is stirred overnight (temperature rises to 45° after 1 hr. then subsides). The solution (750 ml.) and extracted several times with ether. The extract is dried (anhydrous MgSO4) and concentrated by distillation. The residual oil is vacuum distilled to give 276 g. (90%) of trans-2-dimethylaminocyclopentanol, b.p. 98°-100°14 mm; uv (EtOH): end absorption; IR: OH 3370, 3200, N-alkyl 2780, C-O 1045 cm$^{-1}$; mass spectrum: M+ 129; nmr (CDCl3): δvar (br, 1H exchanges with D2O, OH), 3.9-4.3 (m, 1H, CH), 2.3-2.6 (m, 1H, CH), 2.28 (s, 6H, N(CH3)2), 1.2-2.0 (m, 6H, ring hydrogens). The analysis (fumaric acid salt), is given in Table I.

Table I which follows summarizes the physical analytical data for some 2-aminocyclopentanols which were prepared. The particular 2-amino moiety for each such compound is indicated by the indicated group in the -NR1R2 column.

The process utilized to prepare the trans cyclopentane diamine intermediates of this invention is unique and believed to be new or at least an unobvious improvement in that attempts to prepare cyclopentane diamines based on analogy to the cyclohexane diamine chemistry work very inefficiently. More specifically, and for example, the reaction of thionyl chloride with cyclohexane 2-amino-alcohols proceeds smoothly to give the cyclohexane 2-amino halides which proceeds further on reaction with the selected amine to give the cyclohexane 1,2-diamine. In the case of cyclopentane compounds, reaction of thionyl chloride with the amino-alcohol followed by reaction with the selected amine results in only a small yield of the desired cyclopentane diamine; the major product of such reaction is IX, e.g.,

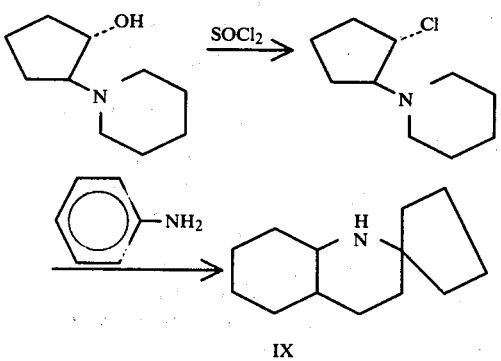

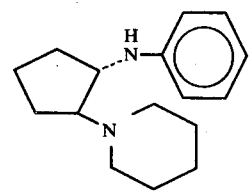

IX whereas, use of methanesulfonyl chloride, as indicated in the above description forms the good leaving group (mesylate) and gives respectable yields of the desired 1,2-cyclopentanediamine precursor to the compounds of this invention. This process is not self-evident on the basis of corresponding cyclohexane ring chemistry.

TABLE I trans-2-aminocyclopentanols

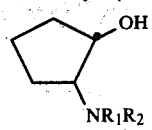

| Starting Materials Number | NR₁R₂ | b.p.(°C.) | m.p.(°C.) | Formula | Analysis Calcd. | | Found | |
|---|---|---|---|---|---|---|---|---|
| A | N(CH$_3$)CH$_2$CH$_3$ | 102°–4°/13 mm | 94°–96° [5,a] | C$_8$H$_{17}$NO . C$_4$H$_4$O$_4$ | C, | 55.58; | C, | 55.92; |
|   |   |   |   |   | H, | 8.16; | H, | 8.17; |
|   |   |   |   |   | N, | 5.40 | N, | 5.54 |
| B | N(CH$_2$CH$_3$)$_2$ | 107°–8°/14 mm | 134°–5° [5,a] | C$_9$H$_{19}$NO . C$_4$H$_4$O$_4$ | C, | 57.12; | C, | 57.20; |
|   |   |   |   |   | H, | 8.48; | H, | 8.54; |
|   |   |   |   |   | N, | 5.13 | N, | 5.10 |
| C | ⌬N (pyrrolidine) | 130°–1°/14 mm | 115°–6° [5,a] | C$_9$H$_{17}$NO . C$_7$H$_7$SO$_3$H | C, | 58.67; | C, | 58.99; |
|   |   |   |   |   | H, | 7.70; | H, | 8.05; |
|   |   |   |   |   | N, | 4.29; | N, | 4.19; |
|   |   |   |   |   | S, | 9.79 | S, | 10.07 |
| D | N(CH$_3$)CH$_2$C$_6$H$_5$ | 134°–40°/0.3 mm | 95°–7° [5,a] | C$_{13}$H$_{19}$NO . C$_4$H$_4$O$_4$ | C, | 63.53; | C, | 63.45; |
|   |   |   |   |   | H, | 7.21; | H, | 7.31; |
|   |   |   |   |   | N, | 4.36 | N, | 4.32 |
| E | N(CH$_3$)CH$_2$CH$_2$C$_6$H$_5$ | 134°–40°/0.3 mm | 139°–41° [5,a] | C$_{14}$H$_{21}$NO . ½ C$_4$H$_4$O$_4$ | C, | 69.28; | C, | 69.25; |
|   |   |   |   |   | H, | 8.36; | H, | 7.31; |
|   |   |   |   |   | N, | 5.05 | N, | 5.12 |
| F | N(CH$_3$)CH$_2$CH=CH$_2$ | 108°–9°/13 mm | — | C$_9$H$_{17}$NO | — | | — | |
| G | N(CH$_3$)$_2$ | 98°/12 mm | 149°–51° [5,a] | C$_7$H$_{15}$NO . ½ C$_4$H$_4$O$_4$ | C, | 57.73; | C, | 57.35; |
|   |   |   |   |   | H, | 9.15; | H, | 9.03; |
|   |   |   |   |   | N, | 7.48 | N, | 7.11 |
| H | N(CH$_3$)CH$_2$CH$_2$N—(CH$_3$)$_2$ | 98°/0.2 mm | 135°–6° [4,a] | C$_{10}$H$_{22}$N$_2$O . C$_4$H$_4$O$_4$ | C, | 51.55; | C, | 51.63; |
|   |   |   |   |   | H, | 7.23; | H, | 7.39; |
|   |   |   |   |   | N, | 6.70 | N, | 6.71 |
| J | N(CH$_3$)CH$_2$CH$_2$CH$_2$N—(CH$_3$)$_2$ | 115°–8°/0.2 mm | 137°–8° [4,a] | C$_{11}$H$_{24}$N$_2$O . C$_4$H$_4$O$_4$ | C, | 52.76; | C, | 53.00; |
|   |   |   |   |   | H, | 7.46; | H, | 7.82; |
|   |   |   |   |   | N, | 6.48 | N, | 6.43 |

Recrystallization solvent
[a]methanol-ether
[b]ethanol-ether
[c]petroleum ether
[d]ether
[e]petroleum ether-ether
[f]benzene
Derivative
[1]free base
[2]hydrochloride
[3]hydrochromide
[4]maleate
[5]fumarate
[6]oxalate
[7]2-naphthalenesulfonate
[8]p-tolueneslfonate
[9]methanesulfonate

II. General procedure for the preparation of trans-1,2-diaminocycloalkanes

The procedure is exemplified by the preparation of trans-N,N-dimethyl-N'-(3,4-dichlorophenyl)-1,2-cyclopentanediamine. Analogs are listed in Table II. All compounds listed have NMR, IR, UV, and mass spectra consistent with the respective structures.

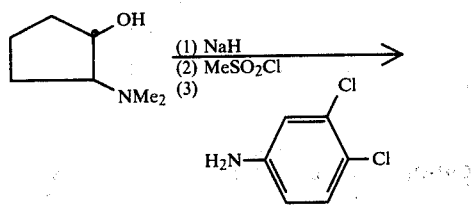

-continued

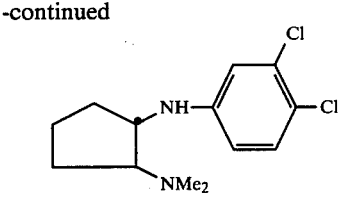

A solution of trans-2-(dimethylamino)cyclopentanol (32.3 g., 0.25 mole) in THF (50 ml.) is added in one portion to a stirred suspension of sodium hydride (10.5 g., 57% dispersion in mineral oil, 0.25 mole) in THF (50 ml.), and the mixture refluxed for 1 hr. The mixture is cooled in ice while methanesulfonyl chloride (28.6 g., 0.25 mole) is added dropwise over 30 min. 3,4-Dichloroaniline (81.0 g., 0.50 mole) is added in one portion when the methanesulfonyl chloride addition is complete. The solvent is removed by distillation, and the residue heated on a steam bath overnight. Sodium hydroxide (200 ml., 20%) is added and heating continued for 1 hr. The mixture is extracted with ether. The organic phase is washed with water and extracted with 10% hydrochloric acid. The aqueous phase is washed with ether, made basic with 40% sodium hydroxide, and extracted with ether. The ether layer is washed with saturated sodium chloride solution, dried (anhydrous MgSO₄) and evaporated. The residual oil is distilled at reduced pressure to give, after a forerun consisting mainly of 3,4-dichloroaniline (65.7 g.), 36.2 g. (53%), 3,4-dichloro-N-[2-(dimethylamino)cyclopentyl]aniline, bp 160°-70°/0.3 mm. The distillate is further purified by formation of the maleic acid salt and recrystallization from methanol-ether; mp 128°-29°; uv (EtOH): $\lambda_{max}$ (ε) 210 (45,450), 257 (19,400), 310 (2300) nm; IR:NH 3380, NH/acid OH 2600, 2520, 2400, $CO_2$/C=C/NH def 1600, 1580, 1480, C—H/C—N/-$CO_2$—1430, 1350, 1330, other 985, 870, 865 cm$^{-1}$; mass spectrum: M⁺ 272, 274 (free base); nmr (D₂O): δ 7.1 (m, 1H, aromatic), 6.7 (m, 1H, aromatic), 6.5 (m, 1H, aromatic), 6.1 (s, 2H, vinyl, maleic acid) 3.8 (m, 1H, CH), 3.35 (m, 1H, CH), 2.75 (s, 6H, N(CH₃)₂), 1.2-2.3 (m, 6H, ring hydrogens).

Anal. Calcd. for $C_{13}H_{18}Cl_2N_2 \cdot C_4H_4O_4$: Calcd.: C, 52.45; H, 5.70; Cl, 18.22; N, 7.20. Found: C, 52.48; H, 5.80; Cl, 18.41; N, 7.07.

TABLE II trans-1,2-diaminocyclopentanes

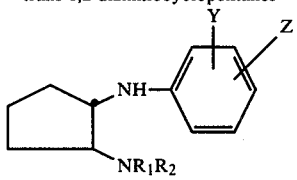

| No. | Y/Z | N R₁R₂ | b.p. (°C.) | m.p.(°C.) | Formula | Analysis Calcd. | | Found |
|---|---|---|---|---|---|---|---|---|
| A | H | N(CH₃)₂ | 97°-103° /0.05 mm | 31°-2° [1] | $C_{13}H_{20}N_2$ | C, | 76.42; | C, 76.42; |
| | | | | | | H, | 9.87; | H, 9.89; |
| | | | | | | N, | 13.71 | N, 13.61 |
| B | 2-CH₃ | N(CH₃)₂ | 120°-5° /0.1 mm | 180°-1° [2,a] | $C_{14}H_{22}N_2 \cdot 2HCl$ | C, | 57.73; | C, 58.51; |
| | | | | | | H, | 8.31; | H, 8.48; |
| | | | | | | Cl, | 24.35; | Cl, 23.19; |
| | | | | | | N, | 9.62 | N, 10.11 |
| C | 3-CH₃ | N(CH₃)₂ | 120°-5° /0.1 mm | 188° [2,a] | $C_{14}H_{22}N_2 \cdot 2HCl$ | C, | 57.73; | C, 57.96; |
| | | | | | | H, | 8.31; | H, 8.26; |
| | | | | | | Cl, | 24.35; | Cl, 24.14; |
| | | | | | | N, | 9.62 | N, 9.88 |
| D | 4-CH₃ | N(CH₃)₂ | 125°-35° /0.1 mm | 198°-200° [2,a] | $C_{14}H_{22}N_2 \cdot 2HCl$ | C, | 57.73; | C, 58.04; |
| | | | | | | H, | 8.31; | H, 8.40; |
| | | | | | | Cl, | 24.35; | Cl, 24.06; |
| | | | | | | N, | 9.62 | N, 9.80 |
| E | 2-Cl | N(CH₃)₂ | 125°-35° /0.1 mm | 93°-5° [4,a] | $C_{13}H_{19}ClN_2 \cdot C_4H_4O_4$ | C, | 57.74; | C, 57.41; |
| | | | | | | H, | 6.53; | H, 6.51; |
| | | | | | | Cl, | 9.99; | Cl, 9.84; |
| | | | | | | N, | 7.90 | N, 7.56 |
| F | 3-Cl | N(CH₃)₂ | 140°-4° /0.2 mm | 125°-7° [4,a] | $C_{13}H_{19}ClN_2 \cdot C_4H_4O_4$ | C, | 57.74; | C, 57.40; |
| | | | | | | H, | 6.53; | H, 6.60; |
| | | | | | | Cl, | 9.11; | Cl, 9.80; |
| | | | | | | N, | 7.90 | N, 8.00 |
| G | 4-Cl | N(CH₃)₂ | 140°-5° /0.2 mm | 41°-2° [1,c] | $C_{13}H_{19}ClN_2$ | C, | 65.39; | C, 65.63; |
| | | | | | | H, | 8.02; | H, 7.99; |
| | | | | | | Cl, | 14.85; | Cl, 14.81; |
| | | | | | | N, | 11.74 | N, 11.88 |
| H | 3-OCH₃ | N(CH₃)₂ | 125°-32° /0.01 mm | 77°-8° [4,a] | $C_{14}H_{22}N_2O \cdot C_4H_4O_4$ | C, | 61.69; | C, 61.69; |
| | | | | | | H, | 7.48; | H, 7.40; |
| | | | | | | N, | 8.00 | N, 7.93 |
| J | 4-OCH₃ | N(CH₃)₂ | 140°-50° /0.3 mm | 85°-7° [4,a] | $C_{14}H_{22}N_2O \cdot C_4H_4O_4$ | C, | 61.69; | C, 61.71; |
| | | | | | | H, | 7.48; | H, 7.47; |
| | | | | | | N, | 8.00 | N, 7.98 |
| K | 3-F | N(CH₃)₂ | 115°-18° /0.3 mm | 137°-8° [4,a] | $C_{13}H_{19}N_2F \cdot C_4H_4O_4$ | C, | 60.34; | C, 60.38; |
| | | | | | | H, | 6.85; | H, 7.00; |
| | | | | | | F, | 5.62; | F, 5.37; |
| | | | | | | N, | 8.28 | N, 8.14 |
| L | 4-F | N(CH₃)₂ | 125°-8° /0.1 mm | 156°-7° [4,a] | $C_{13}H_{19}FN_2 \cdot C_4H_4O_4$ · ½ H₂O | C, | 58.77; | C, 58.80; |
| | | | | | | H, | 6.96; | H, 6.70; |
| | | | | | | F, | 5.47; | F, 5.37; |
| | | | | | | N, | 8.07 | N, 7.85 |
| M | 3-Br | N(CH₃)₂ | 140°-4° /0.3 mm | 114°-15° [4,a] | $C_{13}H_{19}BrN_2 \cdot C_4H_4O_4$ | C, | 51.13; | C, 51.54; |
| | | | | | | H, | 5.81; | H, 5.97; |
| | | | | | | N, | 7.02; | N, 19.74; |
| | | | | | | Br, | 20.02 | Br, 7.02 |
| N | 4-Br | N(CH₃)₂ | 130°-7° /0.1 mm | 44°-5° [1,c] | $C_{13}H_{19}BrN_2$ | C, | 55.13; | C, 55.08; |
| | | | | | | H, | 6.76; | H, 6.84; |
| | | | | | | Br, | 28.22; | Br, 28.43; |
| | | | | | | N, | 9.89 | N, 9.54 |
| P | 4-CH₂CH₃ | N(CH₃)₂ | 125°-30° /0.2 mm | 125°-7° [7,a] | $C_{15}H_{24}N_2 \cdot C_{10}H_8SO_3$ · ½ H₂O | C, | 65.47; | C, 65.87; |
| | | | | | | H, | 7.47; | H, 7.52; |
| | | | | | | N, | 6.11; | N, 6.06; |
| | | | | | | S, | 6.99 | S, 7.14 |
| R | 3,4-diCl | N(CH₃)₂ | 155°-60° /0.3 mm | 128°-9° [4,a] | $C_{13}H_{18}Cl_2N_2 \cdot C_4H_4O_4$ | C, | 52.45; | C, 52.48; |
| | | | | | | H, | 5.70; | H, 5.80; |

TABLE II-continued
trans-1,2-diaminocyclopentanes

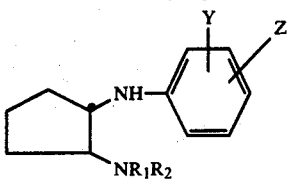

| No. | Y/Z | N R₁R₂ | b.p. (°C.) | m.p.(°C.) | Formula | Analysis Calcd. | | Found | |
|---|---|---|---|---|---|---|---|---|---|
| S | 3,5-diCl | N(CH₃)₂ | —* | 147°–9° [2,a] | C₁₃H₁₈Cl₂N₂ . 2HCl | Cl, | 18.22; | Cl, | 18.41; |
|   |   |   |   |   |   | N, | 7.20 | N, | 7.07 |
|   |   |   |   |   |   | C, | 45.11; | C, | 45.13; |
|   |   |   |   |   |   | H, | 5.82; | H, | 5.72; |
|   |   |   |   |   |   | Cl, | 40.97; | Cl, | 40.46; |
|   |   |   |   |   |   | N, | 8.09 | N, | 7.97 |
| T | 3,4-diCH₃ | N(CH₃)₂ | 170°–80°/0.2 mm | 158°–9° [5,a] | C₁₅H₂₄N₂O₂ . C₄H₄O₄ | C, | 59.93; | C, | 60.21; |
|   |   |   |   |   |   | H, | 7.42; | H, | 7.56; |
|   |   |   |   |   |   | N, | 7.37 | N, | 7.18 |
| U | 3-CF₃ | N(CH₃)₂ | 115°–17°/0.2 mm | 107°–8° [4,a] | C₁₄H₁₉F₃N₂ . C₄H₄O₄ | C, | 55.66; | C, | 55.76; |
|   |   |   |   |   |   | H, | 5.97; | H, | 6.06; |
|   |   |   |   |   |   | F, | 14.68; | F, | 14.50; |
|   |   |   |   |   |   | N, | 7.21 | N, | 7.01 |
| V | 4-CF₃ | N(CH₃)₂ | 116°–20°/0.2 mm | 95°–6° [2,a] | C₁₄H₁₉F₃N₂ . C₁₀H₆SO₃ . ½ H₂O | C, | 58.88; | C, | 58.47; |
|   |   |   |   |   |   | H, | 5.76; | H, | 6.07; |
|   |   |   |   |   |   | F, | 11.64; | F, | 11.47; |
|   |   |   |   |   |   | N, | 5.72; | N, | 5.35; |
|   |   |   |   |   |   | S, | 6.55 | S, | 6.56 |
| W | 3-Cl 4-CH₃ | N(CH₃)₂ | 140°–5°/0.3 mm | 207°–8° [2,a] | C₁₄H₂₁ClN₂ . 2HCl | C, | 51.62; | C, | 51.62; |
|   |   |   |   |   |   | H, | 7.12; | H, | 7.12; |
|   |   |   |   |   |   | Cl, | 32.65; | Cl, | 32.26; |
|   |   |   |   |   |   | N, | 8.59 | N, | 8.60 |
| AA | 4-Cl 3-CH₃ | N(CH₃)₂ | 140°–50°/0.3 mm | 201°–2° [2,a] | C₁₄H₂₁ClN₂ . 2HCl | C, | 51.62; | C, | 51.55; |
|   |   |   |   |   |   | H, | 7.12; | H, | 7.07; |
|   |   |   |   |   |   | Cl, | 32.65; | Cl, | 32.51; |
|   |   |   |   |   |   | N, | 8.59 | N, | 8.53 |
| BB | H | N(CH₃)CH₂—CH₃ | 116°–30°/0.2 mm | 195°–200° [3,a] | C₁₄H₂₂N₂ . 2HBr | C, | 44.23; | C, | 44.14; |
|   |   |   |   |   |   | H, | 6.36; | H, | 6.46; |
|   |   |   |   |   |   | Br, | 42.02; | Br, | 42.29; |
|   |   |   |   |   |   | N, | 7.37 | N, | 7.04 |
| CC | 3,4-diCl | N(CH₂CH₃)₂ | 155°–60°/0.3 mm | 186°–8° [2,a] | C₁₅H₂₂ClN₂ . 2HCl | C, | 48.14; | C, | 48.40; |
|   |   |   |   |   |   | H, | 6.46; | H, | 6.37; |
|   |   |   |   |   |   | Cl, | 37.90; | Cl, | 37.49; |
|   |   |   |   |   |   | N, | 7.49 | N, | 7.70 |
| DD | 3,4-diCl | —N⟨pyrrolidine⟩ | 160°–70°/0.3 mm | 185°–7° [2,a] | C₁₅H₂₀Cl₂N₂ . 2HCl | C, | 48.40; | C, | 48.53; |
|   |   |   |   |   |   | H, | 5.96; | H, | 6.00; |
|   |   |   |   |   |   | Cl, | 38.11; | Cl, | 38.35; |
|   |   |   |   |   |   | N, | 7.53 | N, | 7.44 |
| EE | H | N(CH₃)—CH₂C₆H₅ | 160°–75°/0.25 mm | 109°–10° [2,a] | C₁₉H₂₄H₂ . C₄H₄O₄ | C, | 69.67; | C, | 69.60; |
|   |   |   |   |   |   | H, | 7.12; | H, | 7.43; |
|   |   |   |   |   |   | N, | 7.08 | N, | 6.90 |
| FF | 3,4-diCl | N(CH₃)—CH₂CH=CH₂ | 170°–80°/0.3 mm | 170°–2° [2,a] | C₁₅H₂₀N₂Cl₂ . 2HCl | C, | 48.40; | C, | 48.36; |
|   |   |   |   |   |   | H, | 5.96; | H, | 6.15; |
|   |   |   |   |   |   | N, | 7.53; | N, | 7.54; |
|   |   |   |   |   |   | Cl, | 38.11 | Cl, | 38.36 |
| GG | 3,4-diCl | N(CH₃)CH₂—CH₂N(CH₃)₂ | —* | 161°–2° | C₁₀H₂₅Cl₂N₃ . 2C₄H₄O₄ | C, | 51.25; | C, | 51.33; |
|   |   |   |   |   |   | H, | 5.91; | H, | 6.13; |
|   |   |   |   |   |   | Cl, | 12.61; | Cl, | 12.46; |
|   |   |   |   |   |   | N, | 7.47 | N, | 7.27 |
| HH | 3,4-diCl | N(CH₃)—CH₂CH₂CH₂—N(CH₃)₂ | —* | 155°–7° [4,a] | C₁₇H₂₇Cl₂N₃ . 2C₄H₄O₄ | C, | 52.09; | C, | 51.91; |
|   |   |   |   |   |   | H, | 6.12; | H, | 6.26; |
|   |   |   |   |   |   | Cl, | 12.30; | Cl, | 12.53; |

TABLE II-continued trans-1,2-diaminocyclopentanes

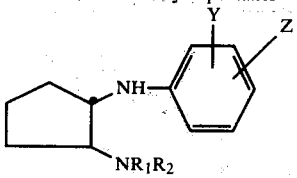

| No. | Y/Z | N R₁R₂ | b.p. (°C.) | m.p.(°C.) | Formula | Analysis Calcd. | Found |
|---|---|---|---|---|---|---|---|
| | | | | | | N, 7.28 | N, 7.23 |

Derivative
[1]free base
[2]hydrochloride
[3]hydrobromide
[4]maleate
[5]fumarate
[6]oxalate
[7]2-naphthalene sulfonate
[8]p-toluenesulfonate
[9]methanesulfonate
Recrystallization Solvent
[a]methanol-ether
[b]ethanol-ether
[c]petroleum ether
[d]ether
[e]petroleum ether-ether
[f]benzene
*isolated by silica gel chromatography

EXAMPLE 1

III. General procedure A for the preparation of trans-N-(2-aminocyclopentyl)anilides, using alkanoic acid anhydride The procedure is exemplified by the preparation of trans-N-[2-(dimethylamino)cyclopentyl]-3',4'-dichloropropionanilide. Analogs are listed in Tables III and IV. All compounds listed have NMR, IR, UV, and mass spectra consistent with the respective structures assigned

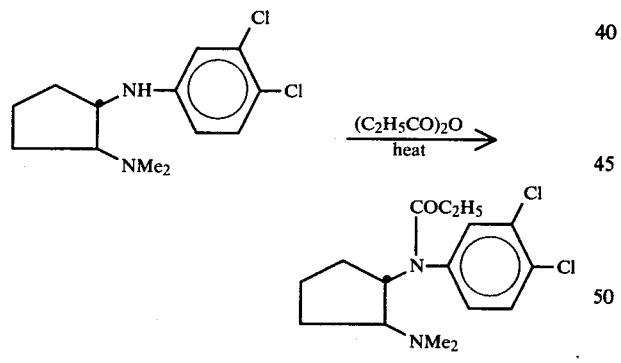

A solution of 3,4-dichloro-N-[2-(dimethylamino)cyclopentyl]aniline (2.73 g., 10.0 mmole) in propionic anhydride (10 ml.) is heated on a steam bath overnight. Water (100 ml.) is added and heating continued for 1 hr. to decompose excess anhydride. The solution is made basic with sodium hydroxide (25 ml., 20% aqueous) and extracted with ether. The extract is washed with saturated sodium chloride solution, dried (MgSO₄) and evaporated to yellow oil. The crude amide product, 3,4-dichloro-N-[2-(dimethylamino)cyclopentyl]propionanilide is purified by formation of the maleic acid salt and recrystallization from methanol-ether; 3.3 g. (74%) mp 154°-5°; uv (EtOH): $\lambda_{max}$ ($\epsilon$) end absorption, 203 (61,350), 264 (sh, 828), 272 (744), 281 (592) nm; IR:NH/acid OH 2720, 2530, 2490, C=O/CO₂⁻/C=C 1665, 1620, 1560 C=O/C—N/other 1355, 1265 1030, 865 cm⁻¹; mass spectrum; M⁺ 328, 330, 332, (free base); nmr (D₂O): δ 7.6 (m, 1H, aromatic), 7.5 (m, 1H, aromatic), 7.3 (m, 1H, aromatic), 6.3 (s, 2H, maleic acid), 5.1 (m, 1H, CH), 3.8 (m, 1H, CH), 2.95 (s, 6H, N⁺(CH₃)₂), 2.0 (q, 2H, CH₃CH₂CO), 1.1-1.9 (m, 6H, ring hydrogens), 0.9 (t, 3H, CH₃CH₂CO).

Anal. Calcd. for C₁₆H₂₂Cl₂N₂O·C₁H₄O₄: Calcd.: C, 53.94; H, 5.89; Cl, 15.95; N, 6.29. Found: C, 53.91; H, 5.82; Cl, 15.82; N, 6.33.

EXAMPLE 2

IV. General procedure B for the preparation of trans-N-(2-aminocyclopentyl)anilides, using alkanoyl halides The procedure is exemplified by the preparation of trans-N-[(2-dimethylamino)cyclopentyl]-4'-(α, α, α-trifluoromethyl)-propionanilide. Analogs are listed in Tables III and IV. All compounds listed have NMR, IR, UV and mass spectra consistent with the respective structures assigned.

A solution of propionyl chloride (2.11 g., 22.0 mmole) in ether (50 ml.) is added dropwise, with ice-cooling, in 30 min. to a solution of the 4-trifluoromethyl-N-[2-(dimethylamino)cyclopentyl]aniline (3.10 g., 11.0 mmole) and triethylamine (2.30 g., 22.0 mmole) in ether (100 ml.). After stirring at room temperature overnight, saturated sodium bicarbonate solution (100 ml.) is added. The organic layer is washed with water and saturated sodium chloride solution, dried (MgSO$_4$) and evaporated to a yellow oil. The crude amide product, 4-trifluoromethyl-N-[2-(dimethylamino)cycloopentyl]-propionanilide is purified by formation of the hydrochloride salt and recrystallization from methanol-ether; 3.20 g. (80%), mp 184°–5°; uv (EtOH): $\lambda_{max}$ ($\epsilon$) end absorption, 231 (sh, 2950), 255 (sh, 1100), 262 (881), 268 (627) nm; IR:N$^+$H 2560, 2460, C=C 1660, C=C 1615, 1585, 1520, CF$_3$/other 1325, 1320, 1175, 1140, 1115, 1075 cm$^{-1}$; mass spectrum: M$^+$ 328 (free base); nmr (D$_2$O): δ7.9 (m, 4H, aromatic), 2.9 (s, 6H, $^+$(CH$_3$)$_2$), 1.4–2.3 (m, 8H, ring hydrogens and CH$_3$CH$_2$CO), 0.9 (t, 3H, CH$_3$CH$_2$CO), other protons not observed due to broadening.

Anal. Calcd. for C$_{17}$H$_{23}$F$_3$N$_2$O·HCl: Calcd: C, 55.96; H, 6.63; Cl, 9.72; F, 15.62; N, 7.68. Found: C, 55.97; H, 6.85; Cl, 9.72; F, 15.48; N, 7.60.

The following Table III summarizes the physical and analytical data for some additional compounds of this invention, and indicates the procedure (A-via alkanoic acid anhydride, or B-via alkanoyl halide) by which the compound is made.

TABLE III trans-N-(2-aminocyclopentyl)-propionanilides

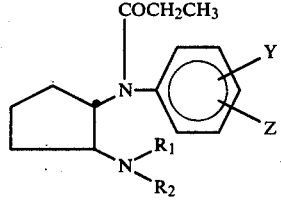

| Example No. | Starting material from Table II | Procedure used A or B | Y/Z | —NR$_1$R$_2$ | mp(°C.) (see footnotes) | Analysis Calcd. | | Found | |
|---|---|---|---|---|---|---|---|---|---|
| 3 | A | A-1 | H | N(CH$_3$)$_2$ | 115°–116°$^{8,a}$ | C, | 62.55; | C, | 62.31; |
| | | | | | | H, | 7.53; | H, | 7.43; |
| | | | | | | N, | 6.34; | N, | 6.32 |
| | | | | | | S, | 7.24; | S, | 7.17 |
| 4 | B | B-1 | 2-CH$_3$ | N(CH$_3$)$_2$ | 129°–130°$^{6,a}$ | C, | 62.62; | C, | 62.82; |
| | | | | | | H, | 7.74; | H, | 7.86; |
| | | | | | | N, | 7.69 | N, | 7.57 |
| 5 | C | A-1 | 3-CH$_3$ | N(CH$_3$)$_2$ | 139°–40°$^{6,a}$ | C, | 62.62; | C, | 62.32; |
| | | | | | | H, | 7.74; | H, | 7.78; |
| | | | | | | N, | 7.69 | N, | 7.66 |
| 6 | D | A-1 | 4-CH$_3$ | N(CH$_3$)$_2$ | 167°–8°$^{7,a}$ | C, | 65.96; | C, | 66.25; |
| | | | | | | H, | 7.18; | H, | 7.03; |
| | | | | | | N, | 5.70; | N, | 5.69; |
| | | | | | | S, | 6.52 | S, | 6.56 |
| 7 | E | B-1 | 2-Cl | N(CH$_3$)$_2$ | 156°7°$^{6,a}$ | C, | 56.17; | C, | 56.09; |
| | | | | | | H, | 6.55; | H, | 6.59; |
| | | | | | | Cl, | 9.21; | Cl, | 9.27; |
| | | | | | | N, | 7.28 | N, | 7.24 |
| 8 | F | A-1 | 3-Cl | N(CH$_3$)$_2$ | 152°–3°$^{6,a}$ | C, | 56.17; | C, | 55.96; |
| | | | | | | H, | 6.55; | H, | 6.60; |
| | | | | | | Cl, | 9.21; | Cl, | 9.12; |
| | | | | | | N, | 7.28 | N, | 7.14 |
| 9 | G | A-1 | 4-Cl | N(CH$_3$)$_2$ | 75°–6°$^{1,c}$ | C, | 65.18; | C, | 12.09; |
| | | | | | | H, | 7.86; | H, | 7.86; |
| | | | | | | Cl, | 12.03; | Cl, | 12.09; |
| | | | | | | N, | 9.50 | N, | 9.42 |
| 10 | H | A-1 | 3-OCH$_3$ | N(CH$_3$)$_2$ | 135°–6°$^{6,a}$ | C, | 59.07; | C, | 58.98; |
| | | | | | | H, | 7.63; | H, | 7.60; |
| | | | | | | N, | 7.07 | N, | 7.17 |
| 11 | J | A-1 | 4-OCH$_3$ | N(CH$_3$)$_2$ | 146°–8°$^{7,a}$ | C, | 65.03; | C, | 64.68; |
| | | | | | | H, | 6.87; | H, | 7.06; |
| | | | | | | N, | 5.62; | N, | 5.70; |
| | | | | | | S, | 6.43 | S, | 6.36 |
| 12 | K | A-1 | 3-F | N(CH$_3$)$_2$ | 85°–8°$^{6,b}$ | C, | 58.02; | C, | 57.97; |
| | | | | | | H, | 6.96; | H, | 6.89; |
| | | | | | | F, | 5.10; | F, | 5.10; |
| | | | | | | N, | 7.29 | N, | 7.51 |
| 13 | L | A-1 | 4-F | N(CH$_3$)$_2$ | 154°–5°$^{7,a}$ | C, | 64.17; | C, | 63.93 |
| | | | | | | H, | 6.42; | H, | 6.65; |
| | | | | | | F, | 3.90; | F, | 3.76; |
| | | | | | | N, | 5.76; | N, | 5.69; |
| | | | | | | S, | 6.59 | S, | 6.83 |
| 14 | M | A-1 | 3-Br | N(CH$_3$)$_2$ | 167°–8°$^{6,a}$ | C, | 50.35; | C, | 50.37; |
| | | | | | | H, | 5.87; | H, | 6.01; |
| | | | | | | Br, | 18.62; | Br, | 18.37; |
| | | | | | | N, | 6.53 | N, | 6.54 |
| 15 | N | A-1 | 4-Br | N(CH$_3$)$_2$ | 78°–9°$^{1,c}$ | C, | 56.64; | C, | 56.85; |
| | | | | | | H, | 6.83; | H, | 7.01; |
| | | | | | | Br, | 23.56; | Br, | 23.39; |
| | | | | | | N, | 8.26 | N, | 8.10 |
| 16 | P | A-1 | 4-CH$_2$CH$_3$ | N(CH$_3$)$_2$ | 154°–6°$^{7,a}$ | C, | 67.71; | C, | 67.40; |
| | | | | | | H, | 7.31; | H, | 7.53; |
| | | | | | | N, | 5.64; | N, | 5.55; |

TABLE III-continued trans-N-(2-aminocyclopentyl)-propionanilides

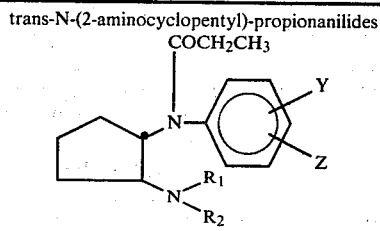

| Example No. | Starting material from Table II | Procedure used A or B | Y/Z | —NR₁R₂ | mp(°C.) (see footnotes) | Analysis Calcd. | | Analysis Found | |
|---|---|---|---|---|---|---|---|---|---|
| 17 | R | A-1 | 3,4-Di-Cl | N(CH$_3$)$_2$ | 154°–5°[4,a] | S, | 6.46 | S, | 6.64 |
|   |   |   |   |   |   | C, | 53.94; | C, | 53.91; |
|   |   |   |   |   |   | H, | 5.89; | H, | 5.82; |
|   |   |   |   |   |   | Cl, | 15.92; | Cl, | 15.82; |
|   |   |   |   |   |   | N, | 6.29 | N, | 6.33 |
| 18 | S | B-1 | 3,5-DiCl | N(CH$_3$)$_2$ | 129°–30°[4,a] | C, | 53.94; | C, | 53.46; |
|   |   |   |   |   |   | H, | 5.89; | H, | 6.04; |
|   |   |   |   |   |   | Cl, | 15.92; | Cl, | 15.78; |
|   |   |   |   |   |   | N, | 6.29 | N, | 6.52 |
| 19 | T | A-1 | 3,4-di-OCH$_3$ | N(CH$_3$)$_2$ | 155°–6°[5,a] | C, | 60.53; | C, | 60.47; |
|   |   |   |   |   |   | H, | 7.39; | H, | 7.38; |
|   |   |   |   |   |   | N, | 6.42 | N, | 6.67 |
| 20 | U | B-1 | 3-CF$_3$ | N(CH$_3$)$_2$ | 135°–6°[6,a] | C, | 54.54; | C, | 54.50; |
|   |   |   |   |   |   | H, | 6.02; | H, | 6.21; |
|   |   |   |   |   |   | F, | 13.62; | F, | 14.09; |
|   |   |   |   |   |   | N, | 6.70 | N, | 6.45 |
| 21 | V | B-1 | 4-CF$_3$ | N(CH$_3$)$_2$ | 184°–5°[2,a] | C, | 55.96; | C, | 55.97; |
|   |   |   |   |   |   | H, | 6.63; | H, | 6.85; |
|   |   |   |   |   |   | Cl, | 9.72; | Cl, | 9.72; |
|   |   |   |   |   |   | F, | 15.62; | F, | 15.48; |
|   |   |   |   |   |   | N, | 7.68 | N, | 7.60 |
| 22 | W | B-1 | 3-Cl, 4-Me | N(CH$_3$)$_2$ | 122°–3°[6,a] | C, | 57.21; | C, | 57.20; |
|   |   |   |   |   |   | H, | 6.82; | H, | 6.84; |
|   |   |   |   |   |   | Cl, | 8.89; | Cl, | 8.84; |
|   |   |   |   |   |   | N, | 7.02 | N, | 6.78 |
| 23 | AA | B-1 | 4-Cl, 3-Me | N(CH$_3$)$_2$ | 131°–2°[6,a] | C, | 57.21; | C, | 57.09; |
|   |   |   |   |   |   | H, | 6.82; | H, | 6.93; |
|   |   |   |   |   |   | Cl, | 8.89; | Cl, | 9.02; |
|   |   |   |   |   |   | N, | 7.02 | N, | 6.99 |
| 24 | CC | A-1 | 3,4-diCl | N(CH$_2$CH$_3$)$_2$ | 148°–9°[9,a] | C, | 50.33; | C, | 50.15; |
|   |   |   |   |   |   | H, | 6.67; | H, | 6.80; |
|   |   |   |   |   |   | Cl, | 15.64; | Cl, | 15.82; |
|   |   |   |   |   |   | N, | 6.18; | N, | 6.06; |
|   |   |   |   |   |   | S, | 7.07 | S, | 6.96 |
| 25 | DD | A-1 | 3,4-diCl | NCH$_2$CH$_2$CH$_2$CH$_2$ (cyclic) | 107°–9°[6,a] | C, | 52.86; | C, | 53.08; |
|   |   |   |   |   |   | H, | 5.99; | H, | 6.01; |
|   |   |   |   |   |   | Cl, | 15.61; | Cl, | 15.73; |
|   |   |   |   |   |   | N, | 6.16 | N, | 6.00 |
| 26 | GG | B-1 | 3,4-diCl | N(CH$_3$)—CH$_2$CH$_2$—N(CH$_3$)$_2$ | 165°–6°[2,a] | C, | 47.81; | C, | 47.52; |
|   |   |   |   |   |   | H, | 6.97; | H, | 6.64; |
|   |   |   |   |   |   | Cl, | 29.72; | Cl, | 29.98; |
|   |   |   |   |   |   | N, | 8.80 | N, | 8.86 |
| 27 | HH | B-1 | 3,4-diCl | N(CH$_3$)—CH$_2$CH$_2$CH$_2$—N(CH$_3$)$_2$ | 259°–60°[2,a] | C, | 50.27; | C, | 50.30; |
|   |   |   |   |   |   | H, | 7.07; | H, | 6.99; |
|   |   |   |   |   |   | Cl, | 29.68; | Cl, | 29.57; |
|   |   |   |   |   |   | N, | 8.79 | N, | 8.52 |
| 28 | R | A-1 | 3-Cl, 4-F | N(CH$_3$)$_2$ | 152°–3°[6,a] | C, | 53.66; | C, | 53.52; |
|   |   |   |   |   |   | H, | 6.00; | H, | 6.13; |
|   |   |   |   |   |   | N, | 6.96; | N, | 6.88; |
|   |   |   |   |   |   | Cl, | 8.80; | Cl, | 8.65; |
|   |   |   |   |   |   | F, | 4.72 | F, | 4.96 |
| 29 | R | A-1 | 3,4-diBr | N(CH$_3$)$_2$ | 146°–7°[6,a] | C, | 42.54; | C, | 42.66; |
|   |   |   |   |   |   | H, | 4.76; | H, | 4.90; |
|   |   |   |   |   |   | N, | 5.51; | N, | 5.71; |
|   |   |   |   |   |   | Br, | 31.45 | Br, | 31.51 |
| 30 | R | A-1 | 3,4-diCH$_3$ | N(CH$_3$)$_2$ | 114°–5°[6,a] | C, | 62.72; | C, | 62.60; |
|   |   |   |   |   |   | H, | 8.03; | H, | 8.14; |
|   |   |   |   |   |   | N, | 7.32 | N, | 7.31 |
| 31 | FF | A-1 | 3,4-diCl | N(CH$_3$)CH$_2$—CH=CH$_2$ | 104°–6°[6,a] | C, | 53.94; | C, | 54.14; |
|   |   |   |   |   |   | H, | 5.87; | H, | 5.88; |
|   |   |   |   |   |   | N, | 6.29; | N, | 6.47; |
|   |   |   |   |   |   | Cl, | 15.92 | Cl, | 15.91 |
| 32 | EE | A-1 | 3,4-diCl | N(CH$_3$)CH$_2$—C$_6$H$_5$ | 120°–1°[6,a] | C, | 56.14; | C, | 56.10; |
|   |   |   |   |   |   | H, | 5.89; | H, | 5.49; |
|   |   |   |   |   |   | N, | 5.46; | N, | 5.25 |
|   |   |   |   |   |   | Cl, | 13.81 | Cl, | 13.26 |

TABLE III-continued
trans-N-(2-aminocyclopentyl)-propionanilides

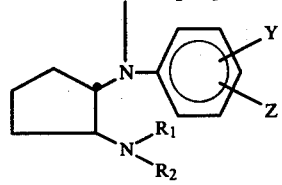

| Example No. | Starting material from Table II | Procedure used A or B | Y/Z | —NR₁R₂ | mp(°C.) (see footnotes) | Analysis Calcd. | | Found | |
|---|---|---|---|---|---|---|---|---|---|
| 33 | H, N(CH₃), CH—CH₂C₆H₅, Cl, Cl | A-1 | 3,4-diCl | N(CH₃)\|CH₂CH₂C₆H₅ | 90°–1°⁶,ᵃ | C, 57.67; H, 6.32; N, 5.17; Cl, 13.09 | | C, 57.52 H, 6.23; N, 4.98; Cl, 12.62 | |
| 34 | H, N(C₃H₇)₂, Cl, Cl | A-1 | 3,4-diCl | N(CH₂CH₂CH₃)₂ | 58°–9°¹,ᶜ | C, 62,33; H, 7.85; N, 7.27; Cl, 18.40 | | C, 62.64; H, 8.02; N, 7.41; Cl, 18.27 | |
| 35 | R | A-1 | 3,4-diCl | N(CH₃)₂ ↓ O | 131°(decomp) g | C, 55.65; H, 6.42; N, 8.12; Cl, 20.54 | | C, 51.19; H, 6.32; N, 7.22; Cl, 22.76 | |
| 36 | *** | A-1 | H | N(CH₃**, CH₃) | 169°–70°²,ᵃ | C, 63.45; H, 8.54; N, 9.25; Cl, 11.70 | | C, 63.51; H, 8.61; N, 9.33; Cl, 11.90 | |
| 37 | see text | A-1 | 3-Cl 4-Cl | N(CH₃**, CH₃) | 171°–3°⁶,ᵃ | C, 51.56; H, 5.77; N, 6.68; Cl, 16.91 | | C, 51.84; H, 5.85; N, 6.66; Cl, 17.11 | |

| Derivative | Recrystallization solvent | Procedure A |
|---|---|---|
| ¹free base | ᵃmethanol-ether | ¹propionic anhydride |
| ²hydrochloride | ᵇethanol-ether | ²acetic anhydride |
| ³hydrobromide | ᶜpetroleum ether | ³butyric anhydride |
| ⁴maleate | ᵈether | Procedure B |
| ⁵fumarate | ᵉpetroleum ether-ether | ¹propionyl chloride |
| ⁶oxalate | ᶠbenzene | ²cyclopropanecarbonyl chloride |
| ⁷2-naphthalenesulfonate | ᵍdioxane | ³acryloyl chloride |
| ⁸p-toluenesulfonate | | ⁴cyclobutanecarbonyl chloride |
| ⁹methanesulfonate | | ⁵cyclohexanecarbonyl chloride |
| | | ⁶isobutynyl chloride |
| | | ⁷ethylchloroformate |
| | | ⁸methoxyacetyl chloride |

*Prepared in manner similar to other diamines of Table II.
**cis configuration
***Follow procedures of Example 37 (text) but substitute equivalent amount of aniline for 3,4-dichloroaniline.

TABLE IV
trans-N-(2-aminocyclopentyl)anilides; Miscellaneous

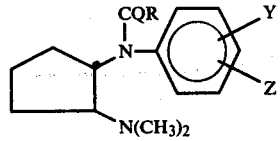

| Example | Starting material from Table II | Y/Z | Procedure | Q | R | mp(°C.)/ see footnote | Formula | Analysis Calcd. | | Found | |
|---|---|---|---|---|---|---|---|---|---|---|---|
| 38 | A | H | A-2 | O | CH₃ | 104°¹,ᵉ | C₁₅H₂₂N₂O | C, 73.13; H, 9.00; N, 11.37 | | C, 73.21; H, 8.96; N, 11.23 | |
| 39 | A | H | A-3 | O | CH₂CH₂\|CH₃ | 115°–16°⁷,ᵃ | C₁₇H₂₆N₂O · C₁₀H₉SO₃ · ½H₂O | C, 66.57; H, 7.14; N, 5.75; S, 6.58 | | C, 66.42; H, 7.13; N, 5.70; S, 6.48 | |
| 40 | R | 3,4-diCl | A-2 | O | CH₃ | 164°–5°⁶,ᵃ | C₁₅H₂₀Cl₂N₂O · C₂H₃O₄ | C, 50.38; H, 5.47; N, 6.91; | | C, 50.28; H, 5.54; N, 6.79; | |

TABLE IV-continued trans-N-(2-aminocyclopentyl)anilides; Miscellaneous

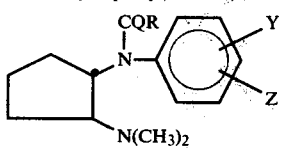

| Example | Starting material from Table II | Y/Z | Procedure | Q | R | mp(°C.)/ see footnote | Formula | Analysis Calcd. | Analysis Found |
|---|---|---|---|---|---|---|---|---|---|
| 41 | R | 3,4-diCl | A-3 | O | CH₂CH₂—CH₃ | 120°-1°⁶,ᵃ | $C_{17}H_{24}Cl_2N_2O \cdot C_2H_2O_9$ | Cl, 17.50; C, 52.66; H, 6.05; N, 6.47; | Cl, 17.29; C, 52.84; H, 6.16; N, 6.69; |
| 42 | R | 3,4-diCl | B-2 | O | ◁ | 145°-6°⁶,ᵃ | $C_{17}H_{22}Cl_2N_2O \cdot C_2H_2O_4 \cdot \tfrac{1}{2} H_2O$ | Cl, 16.36; C, 51.82; H, 5.72; N, 6.36; | Cl, 16.47; C, 51.38; H, 5.62; N, 6.36; |
| 43 | R | 3,4-diCl | B-4 | O | ◇ | 101°-3°⁶,ᵃ | $C_{18}H_{24}Cl_2N_2O \cdot \tfrac{1}{4} Et_2O$ | Cl, 16.10; C, 54.77; H, 6.48; N, 5.81; | Cl, 16.11; C, 54.28; H, 6.38; N, 5.70; |
| 44 | R | 3,4-diCl | B-5 | O | cyclohexyl | 118°-9°¹,ᶜ | $C_{20}H_{28}Cl_2N_2O$ | Cl, 14.70; C, 62.66; H, 7.36; N, 7.31; | Cl, 14.98; C, 62.94; H, 7.50; N, 7.31; |
| 45 | R | 3,4-diCl | B-3 | O | CH=CH₂ | 196°-7°⁶,ᵃ | $C_{16}H_{20}Cl_2N_2O \cdot C_2H_2O_4 \cdot \tfrac{1}{2} H_2O$ | Cl, 18.50; C, 51.25; H, 5.37; N, 6.64; | Cl, 18.59; C, 51.31; H, 5.39; N, 6.61; |
| 46 | R | 3,4-diCl | B-6 | O | CH—(CH₃)₂ | 171°-4°⁶,ᵃ | $C_{17}H_{24}Cl_2N_2O \cdot C_2H_2O_4$ | Cl, 16.81; C, 52.66; H, 6.05; N, 6.47; | Cl, 16.70; C, 52.65; H, 6.15; N, 6.50; |
| 47 | R | 3,4-diCl | A-1 | S | CH₂CH₃ | 192°-4°⁶,ᵃ | $C_{18}H_{22}Cl_2N_2S \cdot C_2H_2O_4$ | Cl, 16.36; C, 49.65; H, 5.56; N, 6.44; Cl, 16.29; S, 7.37 | Cl, 16.26; C, 49.74; H, 5.71; N, 6.40; Cl, 16.46; S, 7.31 |
| 48 | R | 3,4-diCl | B-7 | O | OCH₂—CH₃ | 121°-2°⁶,ᵃ | $C_{16}H_{22}Cl_2N_2O_2 \cdot C_2H_2O_4$ | C, 49.66; H, 5.56; N, 6.44; Cl, 16.29 | C, 49.69; H, 5.74; N, 6.77; Cl, 16.30 |
| 49 | R | 3,4-diCl | B-8 | O | CH₂—OCH₃ | 132°-3°⁶,ᵃ | $C_{16}H_{22}Cl_2N_2O_2 \cdot C_2H_2O_4$ | C, 49.66; H, 5.56; N, 6.44; Cl, 16.29 | C, 49.94; H, 5.53; N, 6.44; Cl, 16.40 |

| Derivative | Recrystallization solvent | Procedure A |
|---|---|---|
| ¹free base | ᵃmethanol-ether | ¹propionic anhydride |
| ²hydrochloride | ᵇethanol-ether | ²acetic anhydride |
| ³hydrobromide | ᶜpetroleum ether | ³butyric anhydride |
| ⁴maleate | ᵈether | Procedure B |
| ⁵fumarate | ᵉpetroleum ether-ether | ¹propionyl chloride |
| ⁶oxalate | ᶠbenzene | ²cyclopropanecarbonyl chloride |
| ⁷2-naphthalenesulfonate | ᵍdioxane | ³acryloyl chloride |
| ⁸p-toluenesulfonate | | ⁴cyclobutanecarbonyl chloride |
| ⁹methanesulfonate | | ⁵cyclohexanecarbonyl chloride |
| | | ⁶isobutynyl chloride |
| | | ⁷ethylchloroformate |
| | | ⁸methoxyacetyl chloride |

*Prepared in manner similar to other diamines of Table II.
**cis configuration
***Follow procedures of Example 37 (text) but substitute equivalent amount of aniline for 3,4-dichloroaniline.

EXAMPLE 35

Preparation of trans-3,4-dichloro-N-[2-(dimethylamino)cyclopentyl]-propionanilide-2-N-oxide Three and five-hundredths grams (0.015 mol) of 85% m-chloroperbenzoic acid in 50 ml. of CHCl₃ is added dropwise over 30 min. to 3.29 g. (0.01 mol) of trans-3,4-dichloro-N-[2-(dimethylamino)cyclopentyl]propionanilide, (prepared in Ex. 1), with ice cooling; the mixture is stirred overnight at room temperature, and is then evaporated to dryness. A viscous oil is obtained; this oil is treated with 50 ml. of ether, and a two-phase system results. This mixture is filtered through 100 g. of silica gel (sintered glass funnel), and eluted with 1500 ml. of ether followed by 500 ml. of MeOH. The MeOH is evaporated to give a residue which is dissolved in warm dioxane, filtered to remove foreign matter, and diluted with ether to the point of cloudiness. Crystals form, and these are recrystallized from dioxane/ether at room temperature. The yield is 0.25 g. (7% yield). NMR (CDCl₃) and IR are consistent with title compound. Analysis and m.p. are in Table IV.

EXAMPLE 37

Preparation of cis-3,4-dichloro-N-[2(dimethylamino)cyclopentyl]propionanilide

Part (A) A solution of 3,4-dichloroaniline (200 g., 1.23 mol), cyclopentene oxide (400 ml.), and conc. HCl (2 ml.) is heated at reflux temperature for 7 days. The unreacted epoxide is evaporated at 60°, and the residue is treated with excess ethereal HCl, and a syrup results. This is washed with 1000 ml. of ether. The residue is crystallized and recrystallized from methanol/ether, (1/5.5, v/v) to give 170.0 g. (49% v yield) of 3,4-dichloro-N-[2-hydroxycyclopentyl]aniline, hydrochloride salt.

Part (B) Propionic anhydride (208 g., 1.6 mol), and the free-base from part (A) (113.2 g., 0.40 mol base) are mixed and heated on a steambath overnight. Water (350 ml.) is added, and heating is continued for 1 hr. After ice cooling, the reaction mixture is neutralized with 240 ml. of 40% NaOH (2.4 mol), and extracted with ether. The ether extract is washed in succession with saturated NaHCO₃, water, 10% HCl, water and saturated NaCl, the organic layer dried over MgSO₄, and then evaporated to a brown oil. Subsequently, this oil is dissolved in 500 ml. 95% EtOH, and 26.4 g. (0.4 mol) of 85% KOH is added. The solution is stirred at room temperature (slight warming) for 3 hr. Evaporation removes the EtOH. The residue is treated with 800 ml. of ether and 250 ml. of water. The organic layer is washed successively with water, 10% HCl, and saturated NaCl, and dried (MgSO₄). The solution is concentrated by distillation and subsequent treatment with petroleum ether results in 87.7 g. (72% yield) of 3,4-dichloro-N-[2-hydroxycyclopentyl]propionanilide.

Part (C) To an ice-cooled solution of 60.4 g. (0.20 mol) of Part (B) product in 1000 ml. of acetone there is added, dropwise, 75 ml. of Jones Reagent (oxidizing). The reaction mixture is stirred at room temperature for 30 min., then is filtered, and the filtrate concentrated at reduced pressure. The residue is dissolved in 500 ml. of ether and this solution is washed three times with water followed by saturated NaCl solution, is dried over MgSO₄ and evaporated to a yellow oil which solidifies on standing. A tacky solid results (44.4 g, 74% yield) which is 3,4-dichloro-N-[2-oxocyclopentyl]propionanilide.

Part (D) A solution of dimethylamine (0.24 mol) and dimethylamine hydrochloride (9.8 g., 0.12 mol) in 250 ml. MeOH is prepared, and 18.0 g. (0.06 mol) of the ketone (from Part (C)) is added all at once. To this mixture is added all at once, 2.65 g. (0.042 mol) of sodium cyanoborohydride and 3A molecular sieves (25 g.). The entire mixture is stirred at room temperature for 8 days, after which time the solution is treated with 10% HCl until gas evolution ceases. Filtration through a filter aid (Celite ®) removes the sieves and a small amount of insoluble matter. The MeOH is evaporated and the remaining aqueous layer, after washing with ether, is made basic with 50 ml. of 40% NaOH, and is filtered to remove amorphous solid. The residue is washed with ether, and the filtrate is extracted with ether. The ether extracts are washed with saturated NaCl solution, dried (MgSO₄) and evaporated to a yellow-brown oil (6.1 g.). Chromatography on 150 g. silica gel (2% MeOH in CHCl₃) gives several 20-ml. fractions; fractions 11–33 (homogeneous by TLC) are combined and evaporated to give 4.2 g. of yellow oil which is converted to the oxalic acid salt in MeOH/ether (1/5, v/v). A solid results (11% yld.), which has a m.p. 171°–3°. This solid is the cis-3,4-dichloro-N[2-(dimethylamino)cyclopentyl]-propionanilide oxalic acid salt. The nmr differs from that of the trans compound (Example 1) in the coupling constant of the 1,2-cyclopentane H's. Also, on TLC on silica gel (EtOAc developing solvent), the free base from this reaction (cis) has a different R$_f$ value than the corresponding trans aminoamide.

Anal. Calcd. for C₁₆H₂₂N₂Cl₂O·C₂H₂O₁: Calcd.: C, 51.56; H, 5.77; N, 6.68; Cl, 16.91. Found: C, 51.84; H, 5.85; N, 6.66; Cl, 17.11.

EXAMPLE 50

Preparation of d- and l-trans-trans-3,4-dichloro-N-[2-dimethylaminocyclopentyl]aniline.

(l-isomer) The di-p-toluoyl-d-tartaric acid salt of the title trans-dl-diamine is prepared by mixing 103.9 g. (0.267 mol) of this tartaric acid with 103.2 g. (0.267 mol) the diamine in a solvent consisting of 500 ml. isopropanol and about 500 ml. of ether. This mixture is seeded with a crystal of the trans-l-diamine, obtained from a small test tube scale resolution preparation, and left to stand. Crystals form; these are collected (75.0 g.) by filtration and recrystallized twice from a mixture of methanol:acetone:ether:2:8:7.5 v/v/v to give 17.5 g. of salt which is converted to the free base with aqueous 20% NaOH, and subsequently to the maleate salt (as in Example 1). Mother liquor saved. Nmr, ir, and mass spectra conform to the assigned structure. m.p. 135°–6°; $[\alpha]_D^{25}$ (MeOH, c.=15.47 mg/2 ml)=−105° to give the l-form of the compound.

Analysis Calcd. for C₁₃H₁₈N₂Cl₂·C₁H₁O₄: Calcd.: C, 52.45; H, 5.70; N, 7.20; Cl, 18.22. Found: C, 52.71; H, 5.76; N, 7.19; Cl, 18.23.

d-isomer The mother liquor from the initial filtration (above) is concentrated under reduced pressure to give a yellow oil which crystallizes in a solvent mixture of MeOH-acetone-ether to give 76.0 g. of crystals; these are then recrystallized twice from methanol-acetone-ether to give 55.0 g. of crystalline material which is converted to the free base and subsequently to the maleic acid addition salt. Spectral data are correct for the assigned structure. m.p. 135°–6°; $[\alpha]_D^{25}$ (MeOH, c.=15.63 mg./2 ml.)=+101° (i.e. the d-isomer).

Anal. Calcd. for C₁₃H₁₈N₂Cl₂·C₄H₄O₄: Calcd.: C, 52.45; H, 5.70; N, 7.20; Cl, 18.22. Found: C, 52.73; H, 5.80; N, 7.28; Cl, 18.47.

EXAMPLE 51

Preparation of d-trans-3,4-dichloro-N-[2-dimethylaminocyclopentane]propionanilide Following the procedure of Example 1, but substituting d-trans-aminoaniline (prepared in Example 50), for the trans-aminoaniline of Example 1 as starting diamine there is obtained the titled compound as the maleic acid addition salt, m.p. 152°–4°. Circular Dichroism [$\theta$]$_{249\mu}{}^{25°}$ +2800±300 (2.5% in 95% EtOH).

Anal. Calcd. for $C_{16}H_{22}N_2Cl_2 \cdot C_4H_4O_4$: Calcd.: C, 53.94; H, 5.89; N, 6.29; Cl, 15.92. Found: C, 54.19; H, 5.91; N, 6.19; Cl, 16.22. [$\theta$]=molecular ellipticity.

Preparation of
1-trans-3,4-dichloro-N-[2-(dimethylamino)cyclopentyl]-propionanilide.

Following the procedure of Example 1 but substituting l-trans-aminoaniline (prepared in Example 50) for the trans-aminoaniline in Example 1, as starting diamine there is obtained the titled compound as the maleic acid addition salt, m.p. 152°–4°. Circular Dichroism [$\theta$]$_{249\mu}{}^{25°}$ −2900±300(2.5% in 95% EtOH).

Anal. Calcd. for $C_{16}H_{22}N_2Cl_2O \cdot C_4H_4O_4$: Calcd.: C, 53.94; H, 5.89; N, 6.29; Cl, 15.92. Found: C, 54.09; H, 5.90; N, 6.54; Cl, 15.82.

EXAMPLE 47

Preparation of
trans-3,4-dichloro-N-[2-(dimethylamino)cyclopentyl]-thiopropionanilide.

A solution of 8.23 g. (0.025 mol) of 3′, 4′-dichloro-N-[2-(dimethylamino)cyclopentyl]propionanilide, (prepared in Example 1) and phosphorus pentasulfide (6.1 g., 0.028 mol) in 250 ml. of pyridine is heated at the reflux temperature overnight. The pyridine is then removed by distillation at ca 100°, in vacuo. The residue is treated with 250 ml. $CHCl_3$ and 200 ml. saturated aqueous sodium bicarbonate and stirred for 1 hr. The organic layer is diluted with 250 ml. of ether and washed successively with 200 ml. of water and 250 ml. of saturated NaCl solution, dried (anhy. $MgSO_4$), and evaporated to a red-brown oil. This oil is triturated twice with hot petroleum ether; a yellow solution and a red solid result. The yellow solution is washed with water, dried ($MgSO_4$), and evaporated to a pale orange oil (3.7 g., 43% yield). The oxalic acid salt is prepared with the oil and 1.0 g. (0.011 mol) of acid in 25 ml. MeOH and 200 ml. ether. On recrystallization, 3.6 g. (33% yield) of the oxalic acid addition salt of the title compound is prepared (see Table IV, Example 47, for analysis and m.p.) Nmr correct for assigned structure.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Rectal suppositories as used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax, (polyoxyethylene glycol) and appropriate mixtures of mono-, di-, and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is about 2.0 gm.

Tablets and capsules for rectal administration are manufactured utilizing the same pharmaceutically acceptable substance and by the same methods as for formulations for oral administration.

Rectal suppositories, tablets or capsules are packaged either individually, in unit-dose, or in quantity, multiple dose, for example, 2, 6, or 12.

The term unit dosage form, as used in the specification and claims, refers to physically discrete units suitable as unitary dosages for mammals including human subjects each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segregated multiples of any of of the foregoing, and other forms as herein described.

The dosage of the compound for treatment depends on route of administration, the age, weight and condition of the patient. A dosage schedule of from about 1 to about 100 mg., preferably 10 to 90 mg. per day, given in a single dose or in subdivided doses, embraces the effective range to alleviate depression for which the compositions are effective. The dosage to be administered is calculated on the basis of from about 0.02 to about 1.5 mg./kg. of weight of the subject. The compound is compounded with a suitable pharmaceutical carrier in unit dosage form for convenient and effective administration. In the preferred embodiments of this invention, the dosage units can contain the compound in 0.5, 1, 5, 10, 20, 30, 50 and 100 mg. amounts for systemic treatment. A sterile preparation of the active material contains 0.1 percent to 25 percent w/v for parenteral treatment. The dosage of compositions containing a compound of formula I and one or more other active ingredients is to be determined with reference to the actual dosage of each such ingredient.

In addition to the administration of a compound of formula I as the principal active ingredient of compositions for treatment of the conditions desired herein, the said compound can be combined with other compounds such as analgesics, for example, aspirin, acetaminophen, PAC compound (phenacetin-aspirin-caffeine), antiinflammatory agents such as ibuprofen, and the like, anxiolytics such as perphenazine, amitriptylene hydrochloride, chlordiazepoxide, alprazolam, doxepin hydrochloride, and the like.

EXAMPLE 52

A lot of 10,000 tablets, each containing 20 mg. of trans-3,4-dichloro-N-[2-(dimethylamino)cyclopentyl]-propionanilide maleate salt, as the active ingredient compound is prepared from the following types and amounts of ingredients:

| | |
|---|---|
| Active ingredient compound | 200 gm. |
| Dicalcium phospate | 1,500 gm. |
| Methylcellulose, U.S.P. (15 cps.) | 60 gm. |
| Talc | 150 gm. |
| Corn Starch | 200 gm. |
| Magnesium stearate | 12 gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in reducing depression in adults at a dose of 1 to 2 tablets per day, depending on the age and weight of the patient.

EXAMPLE 53

One thousand two-piece hard gelatin capsules each containing 10 mg. of 3-bromo-N-[2-(dimethylamino)cyclopentyl]propionanilide, hydrochloride salt as the active ingredient compound are prepared from the following types and amounts of ingredients:

| | |
|---|---|
| Active ingredient compound | 10 gm. |
| Lactose | 75 gm. |
| Talc | 25 gm. |
| Magnesium stearate | 1.5 gm. |

The ingredients are mixed well and filled into capsules of the proper size.

Capsules so prepared are useful for treating depression in adults at a dose of one-two capsules per day.

EXAMPLE 54

One thousand tablets for sublingual use are prepared from the following ingredients:

| | |
|---|---|
| 3-trifluoromethyl-N-[2-(dimethylamino)cyclopentyl]-propionanilide, micronized | 5 gm. |
| Polyethylene glycol 4,000, powdered | 150 gm. |
| Polyethylene glycol 6,000, powdered | 75 gm. |

The ingredients are mixed well and compressed into sublingual-type tablets.

These tablets (each containing 5 mg. of active ingredient) placed under the tongue are useful to reduce depression with a rapid reduction at a dose of 1 tablet per 6 hours.

EXAMPLE 55

Soft gelatin capsules for oral use, each containing 10 mg. of 3,4-dichloro-N-[2-(diethylamino)cyclopentyl]-propionanilide, methanesulfonate salt are prepared by first dispersing the micronized compound in corn oil to render the material capsulatable and then encapsulating in the usual manner. These capsules are useful in treatment of depression at a dose of 1-2 capsules a day.

EXAMPLE 56

One thousand tablets, each containing 30 mg. of 3,4-dichloro-N-[2-(N-pyrrolidinyl)cyclopentyl]propionanilide, salt are made from the following types and amounts of ingredients:

| | |
|---|---|
| 3,4-dichloro-[2-(N-pyrrolidinyl)cyclopentyl]-propionanilide | 30 gm. |
| Lactose | 355 gm. |
| Microcrystalline cellulose NF | 120 gm. |
| Starch | 16 gm. |
| Magnesium stearate powder | 4 gm. |

The ingredients are screened and blended together and pressed into tablets.

The tablets are useful to overcome depression.

EXAMPLE 57

A sterile preparation suitable for intramuscular injection and containing 50 mg. of 3-fluoro-N-[2-(dimethylamino)cyclopentyl]propionanilide, hydrochloride salt, in each milliliter is prepared from the following ingredients:

| | |
|---|---|
| 3-fluoro-N-[2-(dimethylamio)cyclopentyl]-propionanilide, hydrochloride | 50 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected to reduce depression in adults.

EXAMPLE 58

Following the procedure of the preceding Examples 52 through 57, inclusive, unit dosage forms are similarly prepared substituting equivalent amounts of cis or trans variants of other Formula I compounds; for example 3-chloro-4-methyl-N-[2-(dimethylamino)cyclopentyl]propionanilide, 3,4-dichloro-N-[{2-(N-methyl-N-dimethylaminoethyl)amino}cyclopentyl]propionanilide, 3,4-dimethoxy-N-[2-(dimethylamino)cyclopentyl]propionanilide, 3-chloro-4-fluoro-N-[2-(dimethylamino)cyclopentyl]propionanilide, 3,4-dibromo-N-[2-(dimethylamino)cyclopentyl]propionanilide, 3,4-dimethyl-N-[2-(dimethylamino)cyclopentyl]propionanilide, 3,4-dichloro-N-[2-(dimethylamino)cyclopentyl]cyclopropanecarboxanilide, 3,4-dichloro-N-[2-(dimethylamino)cyclopentyl]thiopropionanilide, 3,4-dichloro-N-[2-(N-methyl-N-$\beta$-phenylethylamino)cyclopentyl]propionanilide, 3,4-dichloro-N-[2-(dimethylamino)cyclopentyl]propionanilide, 3-methoxy-N-[2-(dimethylamino)cyclopentyl]propionanilide, 3-chloro-4-methyl-N-[2-dimethylaminocyclopentyl]propionanilide, 3,4-dichloro-N-[2-(diethylamino)cyclopentyl]propionanilide, 3,4-dichloro-N-[2-dimethylaminocyclopentyl]cyclohexanecarboxanilide, or their pharmacologically acceptable acid addition salts for the respective active ingredients in those examples.

I claim:

1. A process for treating depression which comprises administering to a depressed human a compound of the formula

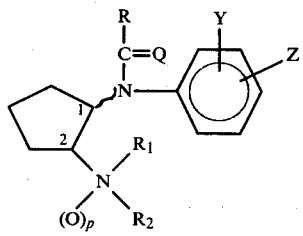

wherein the wavy line ($\sim$) in the 1-position of the cyclopentyl ring indicates cis or trans configuration of the substituents in the 1- and 2-positions of the cyclopentyl ring;

p is zero or 1;

Q is oxygen or sulfur;

R is $C_1$ to $C_3$-alkyl $R_1$ and $R_2$ are taken together with the nitrogen to which they are bonded they complete an N-pyrrolidinyl or N-piperidinyl ring;

each of Y and Z is selected from the group consisting of hydrogen, a halogen having an atomic number of from 9 to 35, trifluoromethyl, $C_1$ to $C_2$-alkyl and $C_1$ to $C_2$-alkyloxy and when Y is trifluoromethyl Z is hydrogen, when Y is $C_1$ to $C_2$-alkyloxy and Z is hydrogen the $C_1$ to $C_2$-alkyloxy is in the 3-position, when Y and Y and Z are both halogens or $C_1$ to $C_2$-alkyloxy they are present in the 3- and 4- or 3- and 5-positions, or a pharmacologically acceptable salt thereof, in an amount in the range from about 1 to about 100 mg. per dosage unit to alleviate the conditions of depression, in association with a pharmaceutical carrier.

2. A process according to claim 1 wherein the formula I compound is one in which R is $C_1$ to $C_3$-alkyl, $R_1$ and $R_2$ are taken together with the nitrogen to which they are bonded to complete an N-pyrrolidinyl or N-piperidinyl moiety, and at least one of Y and Z is a halogen having an atomic number of from 9 to 35, in the 3- or 4-position, or a pharmacologically acceptable salts thereof.

3. A process according to claim 1 wherein the compound is 3,4-dichloro-N-[2-(N-pyrrolidinyl)cyclopentyl]propionanilide, or a pharmacologically acceptable salt thereof.

4. A pharmaceutical preparation in dosage unit form adapted for administration to obtain an anti-depression effect comprising per dosage unit, an anti-depressant effective, non-toxic amount in the range from about 1 to about 100 mg. of a compound of the formula $$\text{(I)}$$

wherein the wave line ($\sim$) in the 1-position of the cyclopentyl ring indicates cis or trans configuration of the substituents in the 1- and 2-positions of the cyclopentyl ring;

p is zero or 1;

Q is oxygen or sulfur;

R is $C_1$ to $C_3$-alkyl;

$R_1$ and $R_2$ are taken together with the nitrogen to which they are bonded they complete an N-pyrrolidinyl or N-piperidinyl ring;

each of Y and Z is selected from the group consisting of hydrogen, a halogen having an atomic number of from 9 to 35, trifluoromethyl, $C_1$ to $C_2$-alkyl and $C_1$ to $C_2$-alkyloxy and when Y is trifluoromethyl Z is hydrogen, when Y is $C_1$ to $C_2$-alkyloxy and Z is hydrogen the $C_1$ to $C_2$-alkyloxy is in the 3-position, when Y and and Z are both halogens or $C_1$ to $C_2$-alkyloxy they are present in the 3- and 4- or 3- and 5-positions, or a pharmacologically acceptable salt thereof, and a pharmaceutical diluent.

5. A pharmaceutical preparation according to claim 4 wherein the compound of formula I is in the trans configuration.

6. A pharmaceutical preparation according to claim 5 wherein the compound of formula I is in the cis configuration.

7. A pharmaceutical preparation according to claim 4 wherein in the formula I compound R is $C_1$ to $C_3$-alkyl, $R_1$ and $R_2$ are taken together with the nitrogen to which they are bonded to complete an N-pyrrolidinyl or N-piperidinyl moiety, and at least one of Y and Z is a halogen having an atomic number of from 9 to 35, in the 3- or 4-position, or a pharmacologically acceptable salt thereof.

8. A pharmaceutical preparation according to claim 7 wherein the formula I compound is 3,4-dichloro-N-[2-(N-pyrrolidinyl)cyclopentyl]propionanilide, or a pharmacologically acceptable salt thereof.

9. 3,4-Dichloro-N-[2-(N-pyrrolidinyl)cyclopentyl]propionanilide, and the pharmacologically acceptable salts thereof.

* * * * *